United States Patent
Medina-Selby

(10) Patent No.: US 8,119,146 B2
(45) Date of Patent: Feb. 21, 2012

(54) EXPRESSING HEPATITIS B VIRUS SURFACE ANTIGEN FOR VACCINE PREPARATION

(76) Inventor: Angelica Medina-Selby, San Francisco, CA (US)

( * ) Notice: Subject to any disclaimer, the term of this patent is extended or adjusted under 35 U.S.C. 154(b) by 818 days.

(21) Appl. No.: 11/918,864

(22) PCT Filed: Apr. 14, 2006

(86) PCT No.: PCT/US2006/014240
§ 371 (c)(1),
(2), (4) Date: Sep. 25, 2008

(87) PCT Pub. No.: WO2006/113528
PCT Pub. Date: Oct. 26, 2006

(65) Prior Publication Data
US 2009/0175904 A1 Jul. 9, 2009

Related U.S. Application Data

(60) Provisional application No. 60/672,838, filed on Apr. 18, 2005.

(51) Int. Cl.
| | |
|---|---|
| *A01N 63/00* | (2006.01) |
| *A61K 39/29* | (2006.01) |
| *A61K 39/12* | (2006.01) |
| *C12N 15/09* | (2006.01) |
| *C12N 15/64* | (2006.01) |
| *C12N 1/00* | (2006.01) |
| *C12N 15/00* | (2006.01) |
| *C12N 15/74* | (2006.01) |
| *C12P 21/04* | (2006.01) |

(52) U.S. Cl. ............... 424/227.1; 424/93.51; 424/189.1; 424/201.1; 424/202.1; 435/320.1; 435/483; 435/254.21; 435/91.4; 435/69.3; 435/71.1

(58) Field of Classification Search .......... None
See application file for complete search history.

(56) References Cited

U.S. PATENT DOCUMENTS

| | | | |
|---|---|---|---|
| 5,639,637 A | 6/1997 | Thomas et al. | |
| 5,928,902 A | 7/1999 | De Wilde et al. | |
| 6,099,840 A * | 8/2000 | Thomas et al. | 424/139.1 |
| 6,103,519 A | 8/2000 | Comberbach et al. | |
| 6,169,171 B1 * | 1/2001 | De Wilde et al. | 536/23.4 |
| 6,306,625 B1 | 10/2001 | Jacobs et al. | |

FOREIGN PATENT DOCUMENTS

EP 0 414 374 A2 2/1991

OTHER PUBLICATIONS

Harford et al., Construction and characterization of a *Saccharomyces cerevisiae* strain (RIT4376) expressing hepatitis B surface antigen, 1987, Postgraduate Medical Journal, vol. 63, Supplemental 2, abstract.*
Jacobs et al., "Simultaneous Synthesis and Assembly of Various Hepatitis B Surface Proteins in *Saccharomyces cerevisiae*" Gene Elsevier Amsterdam, 80:279-291 (1989).
Granoff, D. et al, "Persistence of Group C Anticapsular Antibodies Two to Three Years After Immunization With an . . . " PEDIATR Infect Dis. J, 24 (2): 132-136 (2005).
Aristegui, J. et al, "Comparison of the reactogenicity and immunogenicity of a combined diphtheria, tetanus, acellular pertussis, hepatitis . . . " Vaccine, 21: 3593-3600 (2003).
Hohler, T. et al, "Differential genetic determination of immune responsiveness to hepatitis B surface antigen and to hepatitis A virus . . . " The Lancet, 360: 991-995 (2002).
Rosenberg, S. et al, "Glyceraldehyde-3-phosphate Dehydrogenase-Derived Expression Cassettes for Constitutive Synthesis of . . . " Methods in Enzymology, 185: 341-351 (1990).
Miyanohara, A. et al, "Expression of hepatitis B surface antigen gene in yeast," Proc. Natl. Acad. Sci. USA, 80: 1-5 (1983).
Slack, M. et al, "Immune Response of Premature Infants to Meningococcal Serogroup C and Combined Diphtheria-Tetanus Toxoids-Acellular . . . " J Infect Dis, 184:1617-1620 (2001).
Curran et al., "DTPA-HBV-IPV/HIB Vaccine (Infanrix Hexa)" Drugs, 63(7):673-682 (2003).
http://www.efi-online.de/presse/hexavac.pdf [retired on Mar. 25, 2011] XP-002630094.
Faldella et al., "The Preterm Infant'S Antibody Response to a Combined Diphtheria, Tetanus, Acellular Pertussis and Hepatitis B Vaccine," Vaccine 16(17):1646-1649(1998).

* cited by examiner

*Primary Examiner* — Benjamin P Blumel
(74) *Attorney, Agent, or Firm* — Amy Hessler; Roberta L. Robins; Robert J. Gorman

(57) ABSTRACT

HBsAg is expressed in a *Saccharomyces cerevisiae* host, carrying a plasmid having a HBsAg coding sequence, wherein the plasmid includes: (1) an upstream promoter from a glyceraldehyde-3-phosphate dehydrogenase gene, for controlling expression of the HBsAg coding sequence; and (2) an ARG3 transcription terminator downstream of the HBsAg coding sequence. The plasmids may also include: (3) a LEU2 selection marker; (4) a 2µ plasmid sequence; and (5) an origin of replication functional in *Escherichia coli*. HBsAg can be expressed in this host, and can be purified for use in the manufacture of vaccines, and in particular for the manufacture of combination vaccines and in new monovalent HBV vaccines e.g. with non-alum adjuvants.

33 Claims, No Drawings

EXPRESSING HEPATITIS B VIRUS SURFACE ANTIGEN FOR VACCINE PREPARATION

RELATED APPLICATIONS

This application is a §371 filing of International Application No. PCT/US2006/014240, filed Apr. 14, 2006 and published in English, which claims the benefit under 35 U.S.C. §119(e)(1) of U.S. Provisional Application No. 60/672,838, filed Apr. 18, 2005, from which applications priority is claimed pursuant to the provisions of 35 U.S.C. §§119/120. The teachings of the above applications are incorporated herein in their entirety by reference.

All documents cited herein are incorporated by reference in their entirety.

TECHNICAL FIELD

This invention is in the field of protein expression, in particular for expressing hepatitis B virus surface antigen (HBsAg) for use in preparing vaccines.

BACKGROUND ART

Hepatitis B vaccines have been available for many years (e.g. see chapter 16 of reference 1), and their active ingredient is the surface antigen (HBsAg) from hepatitis B virus (HBV). The original HBV vaccines used HBsAg that had been purified from human blood, but vaccines based on recombinantly-expressed HBsAg became widely available in the 1990s. Since then, HBsAg has also been incorporated as a component in multivalent vaccines i.e. vaccines containing a mixture of immunogens from more than one pathogen, such that administration of the vaccine can simultaneously immunize a subject against more than one pathogen. These multivalent vaccines typically include HBsAg plus at least 'DTP' (diphtheria, tetanus and pertussis) antigens.

The original monovalent recombinant HBV vaccine, ENGERIX B™, includes an aluminum hydroxide adjuvant. More recently, monovalent HBV vaccines based on more modern adjuvants have become available e.g. using the 'AS04' adjuvant [2] in the FENDRIX™ product from GSK, the RC-529 adjuvant in the SUPERVAX™ product from Berna Biotech, or CpG oligonucleotide adjuvants such as CPG7909 [3] from Coley Pharmaceuticals.

For recombinant expression of HBsAg a variety of systems have been described. Expression hosts that have been used include bacteria, yeasts (including *Saccharomyces, Hanensula* and *Pichia* species), mammalian cell culture (including CHO cells, COS cells, Bu3 cells), insect cells (using baculovirus vectors), and plant cells (e.g. for 'edible vaccines').

It is an object of the invention to provide further and improved systems for recombinant expression of HBsAg, particularly for preparing HBsAg to be used in combination vaccines (such as those containing DTP antigens) or in new monovalent HBV vaccines.

DISCLOSURE OF THE INVENTION

Early reports of recombinant HBsAg expression focused on *E. coli [*4-6], mouse cells [7], human cells [8], monkey cells [9] and yeasts [10-12]. More recently, however, expression in recombinant plants has received extensive attention [13-24], as has expression in *Pichia pastoris [*25,26] and *Hanensula polymorpha [*27,28] yeasts.

Despite the move towards these modern expression systems, according to the invention HBsAg is expressed in a

*Saccharomyces cerevisiae* host. Various options are available for yeast-based expression of HBsAg, including choices of yeast species and strain, culture conditions, the promoter used to control expression, gene termination sequences, codon usage, etc. According to the invention, HBsAg is expressed in a *Saccharomyces cerevisiae* host carrying a plasmid having a HBsAg coding sequence, wherein the plasmid includes: (1) an upstream promoter from a glyceraldehyde-3-phosphate dehydrogenase gene, for controlling expression of the HBsAg coding sequence; and (2) an ARG3 transcription terminator downstream of the HBsAg coding sequence. The plasmids will also typically include: (3) a LEU2 selection marker; (4) a 2μ plasmid sequence; and (5) an origin of replication functional in *Escherichia coli.*

HBsAg can be expressed in this *Saccharomyces cerevisiae* host, and can be purified for use in the manufacture of vaccines, and in particular for the manufacture of combination vaccines and in new monovalent HBV vaccines. This yeast-expressed material is suitable for use in these complex vaccines despite the reports in reference 29 that *S. cerevisiae*-expressed HBsAg can have immunosuppressive potential.

Multivalent Vaccines

Thus the invention provides a process for preparing a multivalent immunogenic composition, comprising the steps of: (a) preparing a HBV component by purifying HBsAg after expression in a *S. cerevisiae* host of the invention; (b) preparing at least one non-HBV component; and (c) mixing the HBV and non-HBV components to give the multivalent composition.

The invention also provides a multivalent immunogenic composition comprising: (a) a HBV component comprising HBsAg expressed in a *S. cerevisiae* host of the invention; and (b) at least one non-HBV component. The composition typically also includes one or more adjuvant(s).

These multivalent compositions are particularly useful for simultaneously protecting against infection by HBV and non-HBV pathogens in children. A typical patient will be in the first year of life, and will receive a first dose of the composition between 6 and 9 weeks after birth. Two or three further doses will typically be administered, given at intervals of about 6 to 8 weeks. The composition may also be used to complete the primary immunization schedule of a different vaccine. The composition may also be used as a booster e.g. in children aged 1-16 years.

Monovalent Vaccines

The invention also provides a process for preparing a monovalent immunogenic composition, comprising the steps of: (a) preparing a HBV component by purifying HBsAg after expression in a *S. cerevisiae* host of the invention; (b) combining the HBsAg with an adjuvant to give the immunogenic composition. The adjuvant is preferably not an aluminum hydroxide adjuvant, and is more preferably not solely an aluminum salt adjuvant.

The invention also provides a monovalent immunogenic composition comprising: (a) a HBV component comprising HBsAg expressed in a *S. cerevisiae* host of the invention; and (b) an adjuvant.

These monovalent compositions are particularly useful for protecting against and/or treating hepatitis B virus infections in patients for whom existing adjuvanted vaccines (such as the ENGERIX B™ product) are ineffective. Sub-groups of patients for whom the compositions are particularly suitable include: immunocompromised patients; hemodialysis patients; pre-hemodialysis patients; patients with renal insufficiency; patients with renal failure; patients with early renal failure before they require hemodialysis; patients awaiting liver transplantation e.g. on waiting lists; patients with endstage renal failure; patients who have received an organ transplant (particularly a liver transplant) e.g. in the 6 month period preceding a first dose of the vaccine of the invention; patients who are receiving (or have been receiving e.g. in the 6 month period preceding a first dose of the vaccine of the invention) hepatitis B immunoglobulin (HBIg) treatment; patients with a HLA DQ2 haplotype [30]; patients with a HLA DR3 haplotype [30]; patients with a HLA DR7 haplotype [30]; patients with the with the HLA allele DQB1*0202 [31]; patients infected with HIV; chronic HBV carriers; patients who have recently received a blood transfusion; patients receiving immunosuppressive drugs; patients suffering from AIDS; patients with ascites; patients with cirrhosis; patients with encephalopathy; patients receiving interferon therapy, and in particular ifn-α; patients who smoke cigarettes; patients who smoke cigars; patients with a body mass index ≧30 kg/m², and patients who have received a HBsAg vaccine but who have not seroconverted (e.g. they have a serum anti-HBsAg titer of <10 mIU/ml after a standard primary dosing schedule, such as 3 doses of ENGERIX B™).

These patients may have a creatinine clearance rate of less than 30 ml/min (the normal healthy range being ~100-140 ml/min in males and 90-130 ml/min in females). Patients are preferably at least 15 years old e.g. between 15-40 years, between 15-60 years, between 40-60 years, or even over 60. Patients aged over 55 can usefully be treated regardless of any underlying illness.

The Hepatitis B Surface Antigen

The HBV virion consists of an inner core surrounded by an outer protein coat or capsid. The major component of the capsid is a protein referred to as 'HBsAg'. All existing hepatitis B vaccines contain HBsAg, and when this antigen is administered to a normal vaccinee it stimulates the production of anti-HBsAg antibodies which protect against HBV infection.

For vaccine manufacture, HBsAg can be made in two ways. The first method involves purifying the antigen in particulate form from the plasma of chronic hepatitis B carriers, as large quantities of HBsAg are synthesized in the liver and released into the blood stream during an HBV infection. The second way involves expressing the protein by recombinant DNA methods. HBsAg for use with the present invention is recombinantly expressed in a *Saccharomyces cerevisiae* yeast.

Unlike native HBsAg (i.e. as in the plasma-purified product), HBsAg used with the invention is non-glycosylated. This form of HBsAg is preferred because it is highly immunogenic and can be prepared without the risk of blood product contamination.

The yeast-expressed HBsAg is advantageously in the form of substantially-spherical particles (average diameter of about 20 nm), including a lipid matrix comprising phospholipids. Unlike plasma-derived HBsAg particles, the yeast-expressed particles may include phosphatidylinositol. Moreover, the lipid matrix may include a non-ionic surfactant, such as polysorbate 20, which may be incorporated into the matrix during purification of the antigen from a yeast expression host. Using polysorbate 20 during disruption of recombinant yeast cells at the start of HBsAg purification is one way in which it can be introduced into the HBsAg particles. The polysorbate 20 will typically be present at a weight ratio of at least 5 µg per 100 µg of HBsAg.

All known HBV subtypes contain the common determinant 'a'. Combined with other determinants and subdeterminants, nine subtypes have been identified: ayw1, ayw2, ayw3, ayw4, ayr, adw2, adw4, adrq– and adrq+. Besides these subtypes, other variants have emerged, such as HBV mutants that have been detected in immunised individuals ("escape mutants"). Whereas some studies have found that the majority of sera in non-responders (e.g. in hemodialysis patients) are infected with adw4 or ayw3 subtypes (e.g. see reference 32, where 75% of sera were adw4, rising to 88% in a subset of hemodialysis patients; and reference 33, where 58% of sub-typed samples from hemodialysis patients were ayw3), the most preferred HBV subtype for use with the invention is subtype adw2. This subtype was found in a single hemodialysis patient in reference 32, and in only a small number of outbreaks of HBV infection among hemodialysis patients in California & Nebraska during 1994 [34] and later in Brazil [35,36], but it highly immunogenic and effective in more than 98% of hemodialysis patients.

A preferred HBsAg has the following 226-mer amino acid sequence (SEQ ID NO: 3):

```
MENITSGFLGPLLVLQAGFFLLTRILTIPQSLDSWWTSLNFLGGSPVCLG

QNSQSPTSNHSPTSCPPICPGYRWMCLRRFIIFLFILLLCLIFLLVLLDY

QGMLPVCPLIPGSTTTNTGPCKTCTTPAQGNSMFPSCCCTKPTDGNCTCI

PIPSSWAFAKYLWEWASVRFSWLSLLVPFVQWFVGLSPTVWLSAIWMMWY

WGPSLYSIVSPFIPLLPIFFCLWVYI
```

The invention can use SEQ ID NO: 3, or a sequence differing from SEQ ID NO: 3 by up to 10 (i.e. 1, 2, 3, 4, 5, 6, 7, 8, 9 or 10) single amino acid substitutions.

The HBsAg-coding sequence can be the following 678-mer nucleotide sequence (SEQ ID NO: 4):

```
atggagaacatcacatcaggattcctaggacccctgctcgtgttacaggc ggggttttcttgttgacaagaatcctcacaataccgcagagtctagact cgtggtggacttctctcaattttctaggggatcacccgtgtgtcttggc caaaattcgcagtccccaacctccaatcactcaccaacctcctgtcctcc aatttgtcctggttatcgctggatgtgtctgcggcgttttatcatattcc tcttcatcctgctgctatgcctcatcttcttattggttcttctggattat caaggtatgttgcccgtttgtcctctaattccaggatcaacaacaaccaa tacgggaccatgcaaaacctgcacgactcctgctcaaggcaactctatgt ttccctcatgttgctgtacaaaacctacggatggaaattgcacctgtatt cccatcccatcgtcctgggctttcgcaaaatacctatgggagtgggcctc agtccgtttctcttggctcagtttactagtgccatttgttcagtggttcg tagggctttcccccactgtttggctttcagctatatggatgatgtggtat tgggggccaagtctgtacagcatcgtgagtcccttataccgctgttacc aattttcttttgtctctgggtatacatt
```

The final codon of the HBsAg-coding sequence is preferably followed by a TAA stop codon (ochre).

In addition to the 'S' sequence, a surface antigen may include all or part of a pre-S sequence, such as all or part of a pre-S1 and/or pre-S2 sequence. It is preferred, however, to use only the S sequence, as shown above.

The GAPDH Promoter

According to the invention, HBsAg is expressed in a *Saccharomyces cerevisiae* host carrying a plasmid having an upstream promoter from a glyceraldehyde-3-phosphate dehydrogenase (GAPDH) gene, and in particular from a yeast GAPDH [37-40]. The promoter is linked to the HBsAg-coding sequence in order to regulate its transcription.

Glyceraldehyde-3-phosphate dehydrogenase is a glycolytic enzyme, and its promoter has been found to be particularly suitable for controlling expression of HBsAg in *S. cerevisiae* [41]. The GAPDH promoter disclosed in reference 41 has the following 1061-mer sequence (SEQ ID NO: 5):

aagcttaccagttctcacacggaacaccactaatggacacaaattcgaaa
tactttgaccctattttcgaggaccttgtcaccttgagcccaagagagcc
aagatttaaattttcctatgacttgatgcaaattcccaaagctaataaca
tgcaagacacgtacggtcaagaagacatatttgacctcttaactggttca
gacgcgactgcctcatcagtaagacccgttgaaaagaacttacctgaaaa
aaacgaatatatactagcgttgaatgttagcgtcaacaacaagaagttta
atgacgcggaggccaaggcaaaagattccttgattacgtaagggagtta
gaatcattttgaataaaaaacacgcttttcagttcgagtttatcattat
caatactgccatttcaaagaatacgtaaataattaatagtagtgattttc
ctaactttatttagtcaaaaattagccttttaattctgctgtaacccgta
catgcccaaaataggggggcgggttacacagaatatataacatcgtaggtg
tctgggtgaacagtttatcctggcatccactaaatataatggagctcgc
ttttaagctggcatccagaaaaaaaagaatcccagcaccaaaatattgt
tttcttcaccaaccatcagttcataggtccattctcttagcgcaactaca
gagaacaggggcacaaacaggcaaaaaacgggcacaacctcaatggagtg
atgcaacctgcctggagtaaatgatgacacaaggcaattgacccacgcat
gtatctatctcattttcttacaccttctattaccttctgctctctctgat
ttggaaaaagctgaaaaaaaggttgaaaccagttccctgaaattattcc
cctacttgactaataagtatataaagacggtaggtattgattgtaattct
gtaaatctatttcttaaacttcttaaattctactttatagttagtcttt
tttttagttttaaaacaccaagaacttagtttcgaataaacacacataaa
caaacaagctt This promoter can be used according to the invention, but it is preferred to use a promoter comprising the following 1060-mer nucleotide sequence (SEQ ID NO: 1):

aagcttaccagttctcacacggaacaccactaatggacacacattcgaaa
tactttgaccctattttcgaggaccttgtcaccttgagcccaagagagcc
aagatttaaattttcctatgacttgatgcaaattcccaaagctaataaca
tgcaagacacgtacggtcaagaagacatatttgacctcttaacaggttca
gacgcgactgcctcatcagtaagacccgttgaaaagaacttacctgaaaa
aaacgaatatatactagcgttgaatgttagcgtcaacaacaagaagttta
ctgacgcggaggccaaggcaaaagattccttgattacgtaagggagtta
gaatcattttgaataaaaaacacgcttttcagttcgagtttatcattat
caatactgccatttcaaagaatacgtaaataattaatagtagtgattttc
ctaactttatttagtcaaaaattagccttttaattctgctgtaacccgt
acatgcccaaaataggggggcgggttacacagaatatataacatcgtaggt
gtctgggtgaacagtttattcctggcatccactaaatataatggagcccg
cttttaagctggcatccagaaaaaaaagaatcccagcaccaaaatatt
gttttcttcaccaaccatcagttcataggtccattctcttagcgcaacta
cagagaacaggggcacaaacaggcaaaaaacgggcacaacctcaatggag
tgatgcaacctgcctggagtaaatgatgacacaaggcaattgacccacgc
atgtatctatctcattttcttacaccttctattaccttctgctctctctg
atttggaaaaagctgaaaaaaaggttgaaaccagttccctgaaattatt
cccctacttgactaataagtatataaagacggtaggtattgattgtaatt
ctgtaaatctatttcttaaacttcttaaattctactttatagttagtct
tttttagttttaaaacaccaagaacttagtttcgaataaacacacata
aacaaacaaa This sequence differs from SEQ ID NO: 5 as follows: (1) A/C substitution at nucleotide 42; (2) T/A substitution at nucleotide 194; (3) C/A mutation at nucleotide 301; (4) A insertion at nucleotide 471; (5) C/T substitution at residue 569; (6) T/C substitution at residue 597; (7) T insertion at nucleotide 604 (penta-T instead of tetra-T); and (8) replacement of 3' GCTT sequence with a single A:

The invention can use the SEQ ID NO: 1 promoter sequence, or a sequence differing from SEQ ID NO: 1 by up to 20 (i.e. 1, 2, 3, 4, 5, 6, 7, 8, 9, 10, 11, 12, 13, 14, 15, 16, 17, 18, 19 or 20) point mutations, each point mutation being the deletion, substitution or insertion of a single nucleotide.

The 1060-mer sequence is preferably immediately upstream of the ATG start codon encoding the N-terminus of the HBsAg (SEQ ID NO: 2) e.g.:

aagcttaccagttctcacacggaacaccactaatggacacacattcgaaa
tactttgaccctattttcgaggaccttgtcaccttgagcccaagagagcc
aagatttaaattttcctatgacttgatgcaaattcccaaagctaataaca
tgcaagacacgtacggtcaagaagacatatttgacctcttaacaggttca
gacgcgactgcctcatcagtaagacccgttgaaaagaacttacctgaaaa
aaacgaatatatactagcgttgaatgttagcgtcaacaacaagaagttta
ctgacgcggaggccaaggcaaaagattccttgattacgtaagggagtta
gaatcattttgaataaaaaacacgcttttcagttcgagtttatcattat
caatactgccatttcaaagaatacgtaaataattaatagtagtgattttc
ctaactttatttagtcaaaaattagccttttaattctgctgtaacccgt
acatgcccaaaataggggggcgggttacacagaatatataacatcgtaggt
gtctgggtgaacagtttattcctggcatccactaaatataatggagcccg
cttttaagctggcatccagaaaaaaaagaatcccagcaccaaaatatt
gttttcttcaccaaccatcagttcataggtccattctcttagcgcaacta
cagagaacaggggcacaaacaggcaaaaaacgggcacaacctcaatggag
tgatgcaacctgcctggagtaaatgatgacacaaggcaattgacccacgc
atgtatctatctcattttcttacaccttctattaccttctgctctctctg
atttggaaaaagctgaaaaaaaggttgaaaccagttccctgaaattatt
cccctacttgactaataagtatataaagacggtaggtattgattgtaatt -continued ctgtaaatctatttcttaaacttcttaaattctacttttatagttagtct ttttttagttttaaaacaccaagaacttagtttcgaataaacacacata aacaaacaaaATG . . .

The ARG3 Terminator

According to the invention, HBsAg is expressed in a *Saccharomyces cerevisiae* host carrying a plasmid having an downstream transcription terminator from ARG3. The terminator is linked to the HBsAg-coding sequence in order to regulate its transcription.

The ARG3 gene in yeast encodes the ornithine carbamoyl-transferase enzyme [42] and its transcription termination sequence has been used in several yeast recombinant expression systems [43-45]. It is useful for controlling HBsAg expression in yeast, particularly in combination with a GAPDH promoter.

The sequence immediately downstream of the ARG3 stop codon, as disclosed in GenBank entry GI:171076, is the following 450-mer (SEQ ID NO: 6):

tccttctttcgtgttcttaataactaatatataaatacagatatagatgc atgaataatgatatacattgattattttgcaatgtcaattaaaaaaaaaa aatgttagtaaaactatgttacattccaagcaaataaagcacttggttaa acgaaattaacgttttaagacagccagaccgcggtctaaaaatttaaat atacactgccaacaaattccttcgagttgtccaatttccaccacttttata ttttcatcaacttcagcagattcaaccttctcacatagaacattggaata aacagccttaacaccactttcaagtttgcacagcgtaatatgaggaattt tgttttgacaacacaacccctttaattttctcattgttttcatcaattatg catccatctttatctttagacagttccactacaatagcaatagtttttc Extending 250 nucleotides further backwards into the coding sequence, the ARG3 gene includes the following 700-mer sequence (SEQ ID NO: 7):

agaatttgcgaaacaggccaagctgaaacaattcaaaggttttcaaatca atcaagaacttgtctctgtggctgatccaaactacaaatttatgcattgt ctgccaagacatcaagaagaagttagtgatgatgtcttttatggagagca ttccatagtctttgaagaagcagaaaacagattatatgcagctatgtctg ccatcgatatctttgttaataataaaggtaatttcaaggacttgaaaTAA tccttctttcgtgttcttaataactaatatataaatacagatatagatgc atgaataatgatatacattgattattttgcaatgtcaattaaaaaaaaaa aatgttagtaaaactatgttacattccaagcaaataaagcacttggttaa acgaaattaacgttttaagacagccagaccgcggtctaaaaatttaaat atacactgccaacaaattccttcgagttgtccaatttccaccacttttata ttttcatcaacttcagcagattcaaccttctcacatagaacattggaata aacagccttaacaccactttcaagtttgcacagcgtaatatgaggaattt tgttttgacaacacaacccctttaattttctcattgttttcatcaattatg catccatctttatctttagacagttccactacaatagcaatagtttttc Transcription termination in SEQ ID NO: 7 takes place in the region of the underlined SacII site.

A preferred terminator for use with the invention includes a portion of both the coding and downstream sequences from this ARG3 region, and in particular comprises the following 689-mer nucleotide sequence (SEQ ID NO: 8), which has the same 3' terminus as SEQ ID NO: 7:

cgaattccaagctgaaacaattcaaaggttttcaaatcaatcaagaactt gtctctgtggctgatccaaactacaaatttatgcattgtctgccaagaca tcaagaagaagttagtgatgatgtcttttatggagagcattccatagtct ttgaagaagcagaaaacagattatatgcagctatgtctgccattgatatc tttgttaataataaaggtaatttcaaggacttgaaataatccttctttcg tgttcttaataactaatatataaatacagatatagatgcatgaataatga tatacattgattattttgcaatgtcaattaaaaaaaaaaatgttagtaa aactatgttacattccaagcaaataaagcacttggttaaacgaaattaac gttttaagacagccagaccgcggtctaaaaatttaaatatacactgcca acaaattccttcgagttgtccaatttccaccacttttatattttcatcaac ttcagcagattcaaccttctcacatagaacattggaataaacagccttaa caccactttcaagtttgcacagcgtaatatgaggaattttgttttgacaa cacaacccttaattttctcattgttttcatcaattatgcatccatctttt atctttagacagttccactacaatagcaatagtttttc This sequence usefully includes an EcoRI site near the 5' end (underlined), which facilitates insertion of the terminator into a desired position.

Further downstream terminator sequence from ARG3 can also be present. Up to 1500 nucleotides from ARG3 can be included (i.e. up to a further 800 nucleotides downstream of SEQ ID NO: 7) e.g. up to 1200 nucleotides, or about 1150 nucleotides.

The invention can use the SEQ ID NO: 8 terminator sequence, or a sequence differing from SEQ ID NO: 8 by up to 30 (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) point mutations, each point mutation being the deletion, substitution or insertion of a single nucleotide.

The 689-mer sequence is preferably immediately downstream of the stop codon at the C-terminus of the HBsAg (SEQ ID NO: 9) e.g.:

. . . TAAcgaattccaagctgaaacaattcaaaggttttcaaatcaat caagaacttgtctctgtggctgatccaaactacaaatttatgcattgtct gccaagacatcaagaagaagttagtgatgatgtcttttatggagagcatt ccatagtctttgaagaagcagaaaacagattatatgcagctatgtctgcc attgatatctttgctaataataaaggtaatttcaaggacttgaaataatc cttctttcgtgttcttaataactaatatataaatacagatatagatgcat gaataatgatatacattgattattttgcaatgtcaattaaaaaaaaaaa tgttagtaaaactatgttacattccaagcaaataaagcacttggttaaac gaaattaacgttttaagacagccagaccgcggtctaaaaatttaaatat acactgccaacaaattccttcgagttgtccaatttccaccacttttatatt ttcatcaacttcagcagattcaaccttctcacatagaacattggaataaa -continued

```
cagccttaacaccactttcaagtttgcacagcgtaatatgaggaattttg ttttgacaacacaacccttttaattttctcattgttttcatcaattatgca tccatctttatctttagacagttccactacaatagcaatagtttttc
```

The Plasmid

The gene encoding HBsAg, the GAPDH promoter and the ARG3 terminator are all operatively linked as part of the same plasmid. Plasmids of the invention will also typically include 1, 2 or (preferably) all 3 of the following elements: a LEU2 selection marker; a 2μ plasmid sequence; and an origin of replication functional in *E. coli*. These three components have previously been described in plasmids used for HBsAg expression [45].

The LEU2 selection marker is frequently used in yeast genetics. LEU2 encodes 3-isopropylmalate dehydrogenase, which is the third enzyme in the leucine biosynthesis pathway. The LEU2 marker on the plasmid confers the ability to synthesize leucine from metabolic precursors, and is used in host cells that are leucine auxotrophs e.g. LEU2 null mutants. Thus the LEU2 marker permits a leucine auxotroph, which cannot normally grow without a leucine supply, to grow in the absence of leucine.

The 2μ plasmid sequence is also familiar in yeast genetics [46] and has been used to increase plasmid copy number. Any suitable 2μ plasmid sequence can be used in the plasmids of the invention. The plasmid includes a yeast origin of replication, and this is typically provided by the 2μ sequence.

By including an origin of replication that functions in *E. coli*, plasmids can act as shuttle vectors between yeast and *E. coli*, thereby permitting manipulation of the plasmid in the convenience of *E. coli* systems.

Thus invention provides a plasmid comprising the following elements: (1) a HBsAg coding sequence; (2) a promoter from a glyceraldehyde-3-phosphate dehydrogenase gene, upstream of and for controlling expression of the HBsAg coding sequence; and (3) an ARG3 transcription terminator downstream of the HBsAg coding sequence. The plasmid may also include the following elements: (4) a LEU2 selection marker; (5) a 2μ plasmid sequence; and (6) an origin of replication functional in *E. coli*. The HBsAg coding sequence preferably encodes HBsAg with amino acid sequence SEQ ID NO: 3, or a sequence differing from SEQ ID NO: 3 by up to 10 (i.e. 1, 2, 3, 4, 5, 6, 7, 8, 9 or 10) single amino acid substitutions. The GAPDH promoter sequence preferably comprises SEQ ID NO: 1, or a sequence differing from SEQ ID NO: 1 by up to 20 (i.e. 1, 2, 3, 4, 5, 6, 7, 8, 9, 10, 11, 12, 13, 14, 15, 16, 17, 18, 19 or 20) point mutations. The ARG3 terminator preferably comprises SEQ ID NO: 8, or a sequence differing from SEQ ID NO: 8 by up to 20 (i.e. 1, 2, 3, 4, 5, 6, 7, 8, 9, 10, 11, 12, 13, 14, 15, 16, 17, 18, 19 or 20) point mutations. The plasmid can be maintained in a *S. cerevisiae* host and can be used for expression of HBsAg.

Plasmids with between 14500 and 15000 bp are preferred e.g. between 14600 and 14700 bp.

The *S. Cerevisiae* Host

*Saccharomyces cerevisiae* is a widely-used yeast host for recombinant expression. Any suitable *S. cerevisiae* host can be used with the invention. It is preferred, however, to use a host that is auxotrophic for leucine, such that a LEU2 selection marker can be used in the plasmid. The host cell may be a leu2-3 leu2-112 mutant.

Further characteristics of preferred yeast hosts are his3 and/or can1-11. A most preferred yeast host is leu2-3 leu2-112 his3 can1-11, such as the DC5 strain.

The invention provides a yeast carrying a plasmid of the invention. The invention also provides the use of this yeast in the manufacture of a composition of the invention.

HBsAg Expression and Purification

Techniques for yeast culture for recombinant protein expression are well known in the art. Yeast may be cultured in a synthetic medium e.g. containing purified amino acids (typically omitting leucine where a LEU2 marker is being used), vitamins, salts, etc. HBsAg can then be purified by a process involving steps such as precipitation, ion exchange chromatography, and ultrafiltration. Other steps that may be used during its purification include gel permeation chromatography, and cesium chloride ultracentrifugation.

A particularly preferred step for inclusion in the overall purification process is a step of cell disruption in the presence of a non-ionic detergent, such as Triton-X100 or a fatty acid esters of polyoxyethylene sorbitan, such as polyoxyethylene sorbitan monooleate (also known as polysorbate 80) or, more preferably, polyoxyethylene sorbitan monolaurate (also known as polysorbate 20). The disrupted cells can then be centrifuged to give a supernatant in which the HBsAg is found. The protein can then be purified from the supernatant e.g. using the process disclosed in reference 47.

After purification HBsAg may be subjected to dialysis (e.g. with cysteine), which can be used to remove any mercurial preservatives such as thimerosal that may have been used during HBsAg preparation [48].

HBsAg expressed and purified according to the invention can be combined with further non-HBV antigens to prepare multivalent vaccines, or can be combined with new adjuvants to prepare improved monovalent vaccines.

Monovalent Immunogenic Compositions

HBsAg expressed and purified according to the invention can be combined with new adjuvants to prepare improved monovalent vaccines. Three specific adjuvants of interest for use in monovalent HBV vaccines are: CpG oligonucleotides; aminoalkyl glucosaminide phosphate derivatives; and mixtures of 3d-MPL with aluminum salts.

CpG oligonucleotide adjuvants are immunostimulatory oligonucleotides that include nucleotide sequences containing a CpG motif (a dinucleotide sequence containing an unmethylated cytosine followed by guanosine). Bacterial double stranded RNA or oligonucleotides containing palindromic or poly(dG) sequences have also been shown to be immunostimulatory. The CpG's can include nucleotide modifications/analogs such as phosphorothioate modifications and can be double-stranded or single-stranded. Optionally, the guanosine may be replaced with an analog such as 2'-deoxy-7-deazaguanosine. References 49-51 give examples of possible analog substitutions. The adjuvant effect of CpG oligonucleotides is further discussed in references 52-57.

The CpG sequence may be directed to TLR9, such as the motif GTCGTT (SEQ ID NO: 11) or TTCGTT (SEQ ID NO: 12) [58]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 59-61. Preferably, the CpG is a CpG-A ODN.

Preferably, the CpG oligonucleotide is constructed so that the 5' end is accessible for receptor Preferably, the CpG oligonucleotide is constructed so that the 5' end is accessible for receptor recognition. Optionally, two CpG oligonucleotide sequences may be attached at their 3' ends to form "immunomers". See, for example, refs. 58 & 62-64.

Aminoalkyl glucosaminide phosphate (AGP) derivatives include RC-529 [65-68], which is an aminoalkyl glucosaminide 4-phosphate sold by Corixa Corporation.

AS04 is a mixture of an aluminum salt adjuvant and a 3D-MPL adjuvant [69]. When using AS04, the HBsAg is preferably adsorbed onto the aluminum salt e.g. as described in ref. 70. It is preferred that the aluminum salt is a phosphate, and that at least 50% (by weight) of the total HBsAg is adsorbed to the aluminum phosphate e.g. ≧60%, ≧70%, ≧80%, ≧90%, ≧95%, ≧98% or more. The percentage that is adsorbed can conveniently be measured by separating the adsorbed material from the non-adsorbed material e.g. by centrifugation, in which the aluminum-adsorbed antigen will readily form a pellet, whereas the unadsorbed antigen will remain in the supernatant. The amount of HBsAg in the supernatant (e.g. measured by anti-HBsAg ELISA) can be subtracted from the total amount of HBsAg in the composition, and then the adsorbed percentage can be calculated. It is preferred that the HBsAg is totally adsorbed i.e. none is detectable in supernatant.

The 3D-MPL adjuvant can also be adsorbed onto the aluminum phosphate. Preferably at least 50% (by weight) of the 3D-MPL is adsorbed e.g. ≧60%, ≧70%, ≧80%, ≧90%, ≧95%, ≧98% or more. The percentage that is adsorbed can be measured in the same way as for HBsAg. In a composition having a total 3D-MPL concentration of 50 μg/ml then the concentration of unadsorbed 3D-MPL should be less than 25 μg/ml e.g. ≦20 μg/ml, ≦15 μg/ml, ≦10 μg/ml, ≦5 μg/ml, ≦20 μg/ml, ≦1 μg/ml, etc.

Aluminum phosphate adjuvants are described below in more detail.

3-O-deacylated monophosphoryl lipid A (3D-MPL) has also been referred to as 3 de-O-acylated monophosphoryl lipid A or as 3-O-desacyl-4'-monophosphoryl lipid A. The name indicates that position 3 of the reducing end glucosamine in monophosphoryl lipid A is de-acylated. It has been prepared from a heptoseless mutant of *Salmonella minnesota*, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF. Preparation of 3D-MPL was originally described in reference 71, and the product has been manufactured and sold by Corixa Corporation under the trade name MPL™. Further details can be found in references 72 to 75. The 3D-MPL can be included in combination with a triethanolamine, triethylammonium or triethylamine ion.

3D-MPL can take the form of a mixture of related molecules, varying by their acylation (e.g. having 3, 4, 5 or 6 acyl chains, which may be of different lengths). The two 2-deoxy-2-amino-glucose monosaccharides are N-acylated at their 2-position carbons (i.e. at positions 2 and 2'), and there is also O-acylation at the 3' position. The group attached to carbon 2 has formula —NH—CO—CH$_2$—CR$^1$R$^{1'}$.

The group attached to carbon 2' has formula —NH—CO—CH$_2$—CR$^2$R$^{2'}$. The group attached to carbon 3' has formula —O—CO—CH$_2$—CR$^3$R$^{3'}$. A representative structure is shown below:

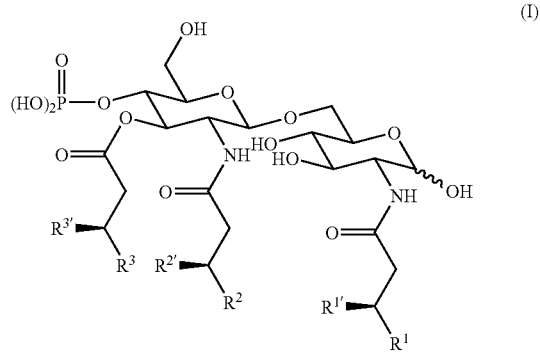

Groups R$^1$, R$^2$ and R$^3$ are each independently —(CH$_2$)$_n$—CH$_3$. The value of n is preferably between 8 and 16, more preferably between 9 and 12, and is most preferably 10.

Groups R$^{1'}$, R$^{2'}$ and R$^{3'}$ can each independently be: (a) —H; (b) —OH; or (c) —O—CO—R$^4$, where R$^4$ is either —H or —(CH$_2$)$_m$—CH$_3$, wherein the value of m is preferably between 8 and 16, and is more preferably 10, 12 or 14. At the 2 position, m is preferably 14. At the 2' position, m is preferably 10. At the 3' position, in is preferably 12. Groups R$^{1'}$, R$^{2'}$ and R$^{3'}$ are thus preferably —O-acyl groups from dodecanoic acid, tetradecanoic acid or hexadecanoic acid.

When all of R$^{1'}$, R$^{2'}$ and R$^{3'}$ are —H then the 3D-MPL has only 3 acyl chains (one on each of positions 2, 2' and 3'). When only two of R$^{1'}$, R$^{2'}$ and R$^{3'}$ are —H then the 3D-MPL can have 4 acyl chains. When only one of R$^{1'}$, R$^{2'}$ and R$^{3'}$ is —H then the 3D-MPL can have 5 acyl chains. When none of R$^{1'}$, R$^{2'}$ and R$^{3'}$ are —H then the 3D-MPL can have 6 acyl chains. The 3D-MPL adjuvant used according to the invention can be a mixture of these forms, with from 3 to 6 acyl chains, but it is preferred to include 3D-MPL with 6 acyl chains in the mixture, and in particular to ensure that the 6 acyl chain form makes up at least 10% by weight of the total 3D-MPL e.g. ≧20%, ≧30%, ≧40%, ≧50% or more. 3D-MPL with 6 acyl chains has been found to be the most adjuvant-active form.

Thus the most preferred form of 3D-MPL for inclusion in compositions of the invention has formula (II), shown below.

In aqueous conditions, 3D-MPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3D-MPL) have been reported to be superior [76] and are preferred for use according to the invention. Preferred particles have a mean diameter less than 220 nm, more preferably less than 200 mm, less than 150 nm, or less than 120 nm. They can even have a mean diameter less than 100 nm. In most cases, however, the mean diameter will not be lower than 50 nm.

Where 3D-MPL is adsorbed to aluminum phosphate then it may not be possible to measure the 3D-MPL particle size directly, but particle size can be measured before adsorption takes place.

Particle diameter can be assessed by the routine technique of dynamic light scattering, which reveals a mean particle diameter. Where a particle is said to have a mean diameter of x nm, there will generally be a distribution of particles about this mean, but at least 50% by number (e.g. ≧60%, ≧70%, ≧80%, ≧90%, or more) of the particles will have a diameter within the range x±20%.

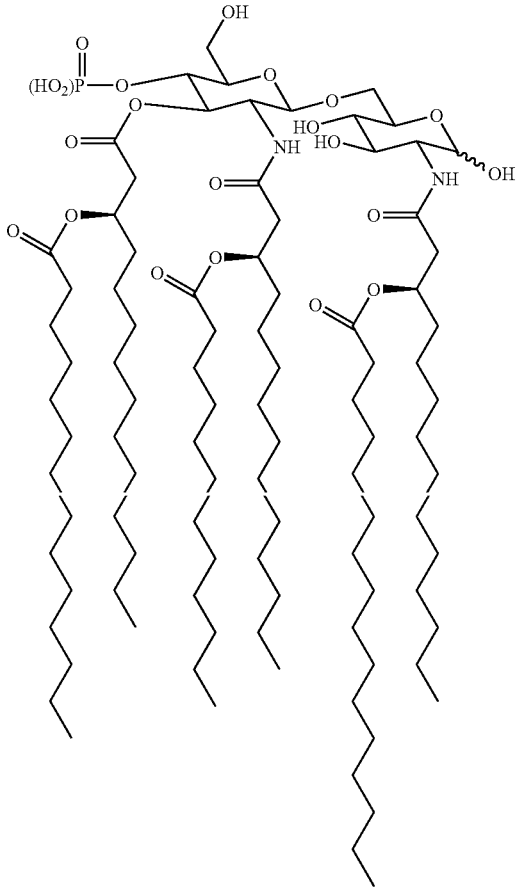

(II)

Multivalent Immunogenic Compositions

HBsAg expressed and purified according to the invention can be combined with one or more non-HBV antigens to prepare multivalent vaccines. The non-HBV antigens can include bacterial and/or viral antigens. Typical non-HBV components for use according to the invention include, but are not limited to:

- a diphtheria toxoid ('D')
- a tetanus toxoid ('T')
- a pertussis antigen ('P'), which may be either cellular ('wP') or acellular ('aP')
- a hepatitis A virus (HAV) antigen
- a conjugated *Haemophilus influenzae* type b capsular saccharide ('Hib')
- inactivated polio virus (IPV)
- a conjugated *Neisseria meningitidis* serogroup C capsular saccharide ('MenC')
- a conjugated *Neisseria meningitidis* serogroup A capsular saccharide ('MenA')
- a conjugated *Neisseria meningitidis* serogroup W135 capsular saccharide ('MenW135')
- a conjugated *Neisseria meningitidis* serogroup Y capsular saccharide ('MenY')
- a conjugated *Streptococcus pneumoniae* capsular saccharide
- a measles virus antigen
- a mumps virus antigen
- a rubella virus antigen
- a varicella zoster virus antigen
- an influenza virus antigen More than one of these non-HBV antigens can be used. The following combinations of antigens are particularly preferred:

Bivalent vaccines: HBV-HAV; HBV-Hib.
Trivalent vaccines: HBV-D-T.
Tetravalent vaccines: HBV-D-T-P.
Pentavalent vaccines: HBV-D-T-P-Hib; HBV-D-T-P-IPV.
Hexavalent vaccines: HBV-D-T-P-Hib-IPV.
Heptavalent vaccines: HBV-D-T-P-Hib-MenA-MenC; HBV-D-T-P-Hib-IPV-MenC.

Diphtheria toxoid ('D') is disclosed in more detail in chapter 13 of reference 1. Preferred diphtheria toxoids are those prepared by formaldehyde treatment. The diphtheria toxoid can be obtained by growing *C. diphtheriae* in growth medium (e.g. Fenton medium, or Linggoud & Fenton medium), which may be supplemented with bovine extract, followed by formaldehyde treatment, ultrafiltration and precipitation. The toxoided material may then be treated by a process comprising sterile filtration and/or dialysis. Quantities of diphtheria toxoid can be expressed in international units (IU). For example, the NIBSC supplies the 'Diphtheria Toxoid Adsorbed Third International Standard 1999' [77,78], which contains 160 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture [79]. For example, the NIBSC supplies 'Diphtheria Toxoid, Plain' [80], which contains 300 LF per ampoule, and also supplies 'The 1st International Reference Reagent For Diphtheria Toxoid For Flocculation Test' [81] which contains 900 Lf per ampoule.

Tetanus toxoid ('T') is disclosed in more detail in chapter 27 of reference 1. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis. Quantities of tetanus toxoid can be expressed in international units (IU). For example, the NIBSC supplies the 'Tetanus Toxoid Adsorbed Third International Standard 2000' [82,83], which contains 469 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture [79]. For example, the NIBSC supplies 'The 1st International Reference Reagent for Tetanus Toxoid For Flocculation Test' [84] which contains 1000 Lf per ampoule.

Pertussis antigen ('P') can be either cellular ('wP') or acellular ('aP'). Cellular pertussis antigens typically take the form of inactivated *B. pertussis* cells. Preparation of cellular pertussis antigens is well documented (e.g. see chapter 21 of reference 1) e.g. it may be obtained by heat inactivation of phase I culture of *B. pertussis*. Quantities of wP antigens can be expressed in international units (IU). For example, the NIBSC supplies the 'Third International Standard For Pertussis Vaccine' [85], which contains 46 IU per ampoule. Each ampoule contains the freeze-dried residue of 2.0 ml aliquots of an aqueous solution which contained 10 liters of bacterial suspension (equivalent to 180 opacity units in terms of the U.S. Opacity Standard) diluted with eight liters of M/15

Sorensen's buffer pH 7.0. As an alternative to the IU system, the 'OU' unit ("opacity units") is also used (e.g. 4 OU may be about 1 IU). Acellular pertussis antigens currently used in vaccines include pertussis toxoid (PT), filamentous haemagglutinin (FHA), pertactin (also known as the '69 kiloDalton outer membrane protein'), and fimbriae (e.g. agglutinogens 2 and 3). The invention preferably uses at least two of, and preferably all three of, PT, FHA and pertactin (i.e. without using fimbriae). These three antigens are preferably prepared by isolation from *B. pertussis* culture grown in modified Stainer-Scholte liquid medium. PT and FHA can be isolated from the fermentation broth (e.g. by adsorption on hydroxyapatite gel), whereas pertactin can be extracted from the cells by heat treatment and flocculation (e.g. using barium chloride). The antigens can be purified in successive chromatographic and/or precipitation steps. PT and FHA can be purified by hydrophobic chromatography, affinity chromatography and size exclusion chromatography. Pertactin can be purified by ion exchange chromatography, hydrophobic chromatography and size exclusion chromatography. FHA and pertactin may be treated with formaldehyde prior to use according to the invention. PT is preferably detoxified by treatment with formaldehyde and/or glutaraldehyde. As an alternative to this chemical detoxification procedure the PT may be a mutant PT in which enzymatic activity has been reduced by mutagenesis [86], but detoxification by chemical treatment is preferred. Quantities of acellular pertussis antigens are typically expressed in micrograms.

Hepatitis A virus (HAV) vaccines are disclosed in chapter 15 of reference 1. A preferred HAV component is based on inactivated virus, and inactivation can be achieved by formalin treatment. Virus can be grown on human embryonic lung diploid fibroblasts, such as MRC-5 cells. A preferred HAV strain is HM175, although CR326F can also be used. The cells can be grown under conditions that permit viral growth. The cells are lysed, and the resulting suspension can be purified by ultrafiltration and gel permeation chromatography.

*H. influenzae* type b capsular saccharide ('Hib') conjugates are disclosed in more detail in chapter 14 of reference 1. The Hib capsular saccharide is conjugated to a carrier protein in order to enhance its immunogenicity, especially in children. Various carrier proteins can be used, including diphtheria toxoid, CRM197, an outer membrane protein complex from serogroup B meningococcus, *H. influenzae* protein D or tetanus toxoid. Tetanus toxoid is the preferred carrier, as used in the product commonly referred to as 'PRP-T'. PRP-T can be made by activating a Hib capsular polysaccharide using cyanogen bromide, coupling the activated saccharide to an adipic acid linker (such as (1-ethyl-3-(3-dimethylaminopropyl)carbodiimide), typically the hydrochloride salt), and then reacting the linker-saccharide entity with a tetanus toxoid carrier protein. The saccharide moiety of a Hib conjugate may comprise full-length polyribosylribitol phosphate (PRP) as prepared from Hib bacteria, and/or it may comprise fragments of full-length PRP. Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. In preferred conjugates, the weight ratio of saccharide to carrier protein is between 1:2.5 and 1:3.5. In vaccines where tetanus toxoid is present both as an antigen and as a carrier protein then the weight ratio of saccharide to carrier protein in the conjugate may be between 1:0.3 and 1:2 [87]. Administration of the Hib conjugate preferably results in an anti-PRP antibody concentration of $\geq 0.15$ µg/ml, and more preferably $\geq 1$ µg/ml, and these are the standard acceptable response thresholds.

Inactivated polio virus vaccine (IPV) is disclosed in more detail in chapter 24 of reference 1. Polioviruses may be grown in cell culture, and a preferred culture uses a Vero cell line, derived from monkey kidney. Vero cells can conveniently be cultured microcarriers. After growth, virions may be purified using techniques such as ultrafiltration, diafiltration, and chromatography. Prior to administration to patients, polioviruses must be inactivated, and this can be achieved by treatment with formaldehyde. Poliomyelitis can be caused by one of three types of poliovirus. The three types are similar and cause identical symptoms, but they are antigenically very different and infection by one type does not protect against infection by others. It is therefore preferred to use three poliovirus antigens in the invention: poliovirus Type 1 (e.g. Mahoney strain), poliovirus Type 2 (e.g. MEF-1 strain), and poliovirus Type 3 (e.g. Saukett strain). The viruses are preferably grown, purified and inactivated individually, and are then combined to give a bulk trivalent mixture for use with the invention. Quantities of IPV are typically expressed in the 'DU' unit (the "D-antigen unit" [88]).

Conjugated meningococcal antigens comprise capsular saccharide antigens from *N. meningitidis* conjugated to carrier proteins. Conjugate vaccines against serogroup C have been approved for human use, and include MENJUGATE™ [89], MENINGITEC™ and NEISVAC-C™. Mixtures of conjugates from serogroups A+C are known [90, 91] and mixtures of conjugates from serogroups A+C+W135+Y have been reported [92-95] and were approved in 2005 as the MENACTRA™ product. The meningococcal saccharide(s) used in the invention can be from one or more of serogroups A, C, W135 and Y e.g. A+C, A+W135, A+Y, C+W135, C+Y, W135+Y, A+C+W135, A+C+Y, C+W135+Y, A+C+W135+Y. It is preferred to use at least the serogroup C saccharide, and preferably to use the saccharides from both of serogroups A and C. The MENJUGATE™ and MENINGITEC™ products use a CRM197 carrier protein, and this carrier can also be used according to the invention. The NEISVAC-C™ product uses a tetanus toxoid carrier protein, and this carrier can also be used according to the invention, as can diphtheria toxoid. A particularly preferred carrier protein for the meningococcal conjugates is protein D from *H. influenzae*, which is not present in any existing approved conjugate vaccines. The saccharide moiety of the conjugate may comprise full-length saccharides as prepared from meningococci, and/or it may comprise fragments of full-length saccharides. Serogroup C saccharides may be prepared from either OAc+ or OAc− strains. For serogroup A saccharides, preferably at least 50% (e.g. at least 60%, 70%, 80%, 90%, 95% or more) of the mannosamine residues are O-acetylated at the C-3 position. Meningococcal conjugates with a saccharide:protein ratio (w/w) of between 1:10 (i.e. excess protein) and 10:1 (i.e. excess saccharide) may be used e.g. ratios between 1:5 and 5:1, between 1:2.5 and 2.5:1, or between 1:1.25 and 1.25:1. Administration of a conjugate preferably results in an increase in serum bactericidal assay (SBA) titre for the relevant serogroup of at least 4-fold, and preferably at least 8-fold. SBA titres can be measured using baby rabbit complement or human complement [96].

Conjugated pneumococcal antigens comprise capsular saccharide antigens from *S. pneumoniae* conjugated to carrier proteins [e.g. refs. 97 to 99]. It is preferred to include saccharides from more than one serotype of *S. pneumoniae*: mixtures of polysaccharides from 23 different serotype are widely used, as are conjugate vaccines with polysaccharides from between 5 and 11 different serotypes [100]. For example, PrevNar™ [101] contains antigens from seven serotypes (4, 6B, 9V, 14, 18C, 19F, and 23F) with each saccharide individually conjugated to $CRM_{197}$ by reductive amination, with 2 µg of each saccharide per 0.5 ml dose (4 µg of serotype 6B), and with conjugates adsorbed on an aluminum phosphate adjuvant. Compositions of the invention preferably include at least serotypes 6B, 14, 19F and 23F. Further serotypes are preferably selected from: 1, 3, 4, 5, 7F, 9V and 18C.

Antigens for protecting against measles, mumps and rubella viruses are typically live viruses, as found in known monovalent and trivalent ('MMR') vaccines. Measles virus vaccines are described in more detail in chapter 19 of reference 1. Mumps virus vaccines are described in more detail in chapter 20 of reference 1. Rubella virus vaccines are described in more detail in chapter 26 of reference 1. Typical measles virus strains include: Moraten; Connaught; Schwarz; Edmonston-Zagreb; CAM-70; AIK-C; TD97; Leningrad-16; Shanghai-191; etc. The Schwarz and Moraten strains are most common for use in USA and Europe. Typical mumps virus strains include: Jeryl Lynn; RIT 4385; Urabe; Hoshino; Rubini; Leningrad-3; Leningrad-Zagreb; Miyahara; Torii; NK M-46; S-12; etc. The Jeryl Lynn, RIT 4385, Urabe and Leningrad-Zagreb strains are the most common worldwide strains. Typical rubella virus strains include: RA27/3; Matsuba; TCRB 19; Takahashi; Matsuura; TP-336; etc. The RA27/3 strain is the most common strain used in the western world.

VZV antigens for protecting against chickenpox are typically live viruses, based on the Oka strain of the virus. VZV vaccines are described in more detail in chapter 28 of reference 1.

Influenza virus antigens are described in more detail in chapters 17 & 18 of reference 1. Broadly, influenza virus vaccines can be based on live virus or inactivated virus, and inactivated vaccines can be based on whole virus, 'split' virus or on purified surface antigens (including hemagglutinin and neuraminidase). The viruses used to prepare the vaccines can be grown either on eggs or on cell culture. Vaccine strains for influenza virus change from season to season. In the current inter-pandemic period, vaccines typically include two influenza A strains (H1N1 and H3N2) and one influenza B strain, and trivalent vaccines are typical. The invention may also use viruses from pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. The influenza virus may be a reassortant strain, and may have been obtained by reverse genetics techniques. The virus may be attenuated. The virus may be temperature-sensitive. The virus may be cold-adapted.

When making multivalent combinations, antigens can be combined individually in series, or they can be pre-mixed and added together. For example, a 4-valent DTP-HBsAg vaccine can be made by a process involving serial addition of HBsAg, D, T and P antigens to a vessel, or by pre-mixing D, T and P antigens and then combining the HBsAg and the DTP mixture.

Antigenic components can be combined in any suitable order.

Where diphtheria and tetanus toxoids are included in a composition of the invention, they are preferably pre-mixed before being combined with HBsAg. Thus the process of the invention involves combining a first component comprising HBsAg with a second component comprising both D and T antigens. Thus it is preferred to use a pre-mixed D-T component. This bivalent component can be used in the processes of the invention e.g. it can be combined with HBsAg to make a trivalent D-T-HBV component. As an alternative, the pre-mixed D-T component can be combined with further non-HBV antigens (e.g. with acellular pertussis antigens), and that component can then be combined with HBsAg, etc.

Similarly, where diphtheria toxoid, tetanus toxoid and whole cell pertussis antigens are included in a composition, they are preferably pre-mixed, and so the process of the invention involves combining a first component comprising HBsAg with a second component comprising D, T and Pw antigens.

Thus it is preferred to use a pre-mixed D-T-Pw component, and then to use this component during the processes of the invention.

When an adjuvant is included in the compositions of the invention, this also can be added at various stages. Typically, antigens will have been combined with adjuvants before being used in the processes of the invention (e.g. a bivalent D-T mixture will have been adsorbed to aluminum salt adjuvant(s) before being used in the processes of the invention), but it is also possible to add adjuvant after the antigens have been mixed, or to add the antigens to an adjuvant (e.g. to start with an aqueous adjuvant, then to add antigens, either individually or pre-mixed). As described below, the HBsAg component is preferably adsorbed to an aluminum phosphate adjuvant before being combined with the non-HBV antigenic components.

HBsAg Fusion Proteins

As well as being used to express HBsAg, the invention can be used to express hybrid antigens that include a HBsAg sequence and a non-HBsAg sequence within the same polypeptide. The non-HBsAg sequence may be inserted into the HBsAg sequence, or may be fused to the N-terminus or C-terminus of the HBsAg sequence.

It is known to fuse the HBsAg sequence to heterologous antigens to exploit HBsAg's ability to assemble into particles. For example, reference 102 reports fusions of HIV-1 gp120 to HBsAg to give a protein that spontaneously assembled into particles that resemble native HBsAg particles in size and density, consistent with a lipid composition of about 25% and a gp120 content of about 100 per particle. The gp120 was able to folds into its native conformation in the fusion, and retained its biological activity. Similarly, HIV gp41 epitopes have been improved by making internal fusions with HBsAg, and the fusion protein self-assembled in yeast into 22 nm lipoprotein particles [103].

This approach has also been used for malaria vaccines. Reference 104 reports that epitopes of up to 61aa from the malaria gp190 antigen were inserted into the HBsAg sequence, and that the expressed hybrid particles could elicit an anti-gp190 immune response in animals. Reference 105 report an protein having 16 repeats of a 4-mer sequence of the circumsporozoite protein expressed as a fusion protein with HBsAg. Reference 106 reports the production in yeast of virus-like particles composed of Pfs16 fused to HBsAg. Reference 107 discloses a hybrid antigen in which the circumsporozoite protein is fused to HBsAg. Reference 108 discloses a fusion of the C-terminal region of the merozoite surface 1 protein of *P. vivax*, which formed immunogenic particles of 20-45 nm size. The use of HBsAg for presenting malarial antigens in self-assembling particulate form is therefore well known in the art.

This approach is particularly suitable for fusing HBsAg sequences with antigens from HIV, *Plasmodium falciparum, Plasmodium vivax, Plasmodium malariae* or *Plasmodium ovale*. Suitable HIV antigens for making HBsAg hybrids include envelope glycoprotein gp120 or antigenic fragments thereof [102]. Suitable *P. falciparum* antigens for making HBsAg hybrids may be based on a subunit of the circumsporozoite surface antigen ("CSP") e.g. they may include between 3 and 20 repeats of its NANP motif (SEQ ID NO: 14), and/or they may include the C-terminal region of CSP (but typically not including the final 12 amino acids from the C-terminal). For example, the invention may use the antigen known as "RTS", which contains a large portion of the C-terminal of CSP from the NF54 or 7G8 isolate of *P. falciparum* (amino acids 210 to 398, which includes 19 NANP repeats and the T cell epitope region at amino acids 367 to 390), fused to the N-terminus of HBsAg by four amino acids of the preS2 portion of HBsAg. When expressed in yeast, RTS forms particles that include lipids (primarily phospholipid) in addition to protein. The sequence of RTS can thus, as in SEQ ID NO: 15 herein, contain: (i) a N-terminus methionine residue; (ii) Met-Ala-Pro; (iii) 189 amino acids corresponding either to amino acids 210-398 of CS protein from *P. falciparum* 7G8 or to amino acids 207-395 of CS protein from *P. falciparum* NF54; (iv) Arg or Gly; (v) Pro-Val-Thr-Asn from hepatitis B Pre-S2 protein; and (vi) HBsAg. From the 7G8 isolate, full-length RTS has the sequence given as SEQ ID NO: 1 in reference 109 (see also FIG. 5 of reference 110):

```
MMAPDPNANPNANPNANPNANPNANPNANPNANPNANPNANPNANPNANP

NANPNANPNANPNANPNANPNANPNANPNANPNKNNQGNGQGHNMPNDPN

RNVDENNANNAVKNNNNEEPSDKHIEQYLKKIKNSISTEWSPCSVTCGNG

IQVRIKPGSANKPKDELDYENDIEKKICKMEKCSSVFNVVNSRPVTNMEN

ITSGFLGPLLVLQAGFFLLTRILTIPQSLDSWWTSLNFLGGSPVCLGQNS

QSPTSNHSPTSCPPICPGYRWMCLRRFIIFLFILLLCLIFLLVLLDYQGM

LPVCPLIPGSTTTNTGPCKTCTTPAQGNSMFPSCCCTKPTDGNCTCIPIP

SSWAFAKYLWEWASVRFSWLSLLVPFVQWFVGLSPTVWLSAIWMMWYWGP

SLYSIVSPFIPLLPIFFCLWVYI
```

This hybrid antigen can be expressed in yeast, using a sequence encoding SEQ ID NO:15. It is preferred to co-express the hybrid protein in yeast with normal HBsAg. This approach has previously been used with RTS, and the product of co-expression is referred to as "RTS,S". A RTS:S ratio of about 1:4 is useful.

Thus a useful aspect of the present invention is to co-express (i) HBsAg and (ii) RTS. One or both of these antigens may be expressed using the plasmids described hereinabove. The co-expressed proteins form a particulate antigen that can be used as an active ingredient in a malaria vaccine.

Adjuvants for Use in Multivalent Vaccines

'Modern' adjuvants including CpG, AGPs and AS04 are described above. While these can be used in multivalent compositions of the invention, it is preferred instead to use aluminum salts. These include the adjuvants known as aluminum hydroxide and aluminum phosphate. These names are conventional, but are used for convenience only, as neither is a precise description of the actual chemical compound which is present [e.g. see chapter 9 of reference 111]. The invention can use any of the "hydroxide" or "phosphate" adjuvants that are in general use as adjuvants.

The adjuvants known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as aluminum hydroxide Al(OH)$_3$, by infrared (IR) spectroscopy, in particular by the presence of an adsorption band at 1070 cm$^{-1}$ and a strong shoulder at 3090-3100 cm$^{-1}$ [chapter 9 of ref. 111].

The adjuvants known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls [ch. 9 of ref. 111].

The PO$_4$/Al$^{3+}$ molar ratio of an aluminum phosphate adjuvant will generally be between 0.3 and 1.2, preferably between 0.8 and 1.2, and more preferably 0.95±0.1. The aluminum phosphate will generally be amorphous, particularly for hydroxyphosphate salts. A typical adjuvant is amorphous aluminum hydroxyphosphate with PO$_4$/Al molar ratio between 0.84 and 0.92, included at 0.6 mg Al$^{3+}$/ml. The aluminum phosphate will generally be particulate. Typical diameters of the particles are in the range 0.5-20 μm (e.g. about 5-10 μm) after any antigen adsorption.

The PZC of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5 e.g. about 5.7.

An aluminum phosphate solution used to prepare a composition of the invention may contain a buffer (e.g. a phosphate or a histidine or a Tris buffer), but this is not always necessary. The aluminum phosphate solution is preferably sterile and pyrogen-free. The aluminum phosphate solution may include free aqueous phosphate ions e.g. present at a concentration between 1.0 and 20 mM, preferably between 5 and 15 mM, and more preferably about 10 mM. The aluminum phosphate solution may also comprise sodium chloride. The concentration of sodium chloride is preferably in the range of 0.1 to 100 mg/ml (e.g. 0.5-50 mg/ml, 1-20 mg/ml, 2-10 mg/ml) and is more preferably about 3±1 mg/ml. The presence of NaCl facilitates the correct measurement of pH prior to adsorption of antigens.

Aluminum salts can be used for adsorption of any of the HBV and non-HBV antigens. HBsAg is preferably adsorbed to an aluminum phosphate adjuvant [70]. Diphtheria toxoid is preferably adsorbed to an aluminum hydroxide adjuvant. Tetanus toxoid is preferably adsorbed to an aluminum hydroxide adjuvant, but this is not necessary (e.g. adsorption of between 0-10% of tetanus toxoid can be used). Acellular pertussis antigens, and particularly the 69 kDa antigen, are preferably adsorbed to an aluminum hydroxide adjuvant. Conjugated Hib antigens can be adsorbed to aluminum phosphate [112,113] or can be unadsorbed. Hib adsorption in this way is particularly useful in vaccines comprising D-T-Pw-Hib-HBsAg antigens Other conjugated antigens (e.g. meningococcus, pneumococcus) can similarly be adsorbed to an aluminum salt (e.g. a phosphate) or can be unadsorbed [114]. IPV antigens are typically not adsorbed to any adjuvant before being used in a process of the invention, but they can become adsorbed onto aluminum adjuvant(s) originating with other components.

For HBsAg adsorption, an aluminum phosphate adjuvant is preferably used in the form of an aqueous solution to which HBsAg is added (NB: it is standard to refer to aqueous aluminum phosphate as a "solution" although, on a strict physicochemical view, the salt is insoluble and forms a suspension). It is preferred to dilute the aluminum phosphate to the required concentration and to ensure a homogenous solution before the addition of the HBsAg. The concentration of $Al^{3+}$ prior to addition of HBsAg is generally between 0 and 10 mg/ml. A preferred $Al^{3+}$ concentration is between 2 and 6 mg/ml.

Two preferred components for use in the processes of the invention are: (1) a bivalent D-T component, comprising an aluminum hydroxide adjuvant; and (2) a trivalent D-T-Pw component, comprising both aluminum hydroxide and aluminum phosphate adjuvants.

Pharmaceutical Compositions

In addition to the adjuvant and antigen components, compositions of the invention may include further components. These components may have various sources. For example, they may be present in one of the antigen or adjuvant components that is used during manufacture or may be added separately from the antigenic components.

Preferred compositions of the invention include one or more pharmaceutical carrier(s) and/or excipient(s).

To control tonicity, it is preferred to include a physiological salt, such as a sodium salt. Sodium chloride (NaCl) is preferred, which may be present at between 1 and 20 mg/ml.

Compositions will generally have an osmolality of between 200 mOsm/kg and 400 mOsm/kg, preferably between 240-360 mOsm/kg, and will more preferably fall within the range of 290-300 mOsm/kg. Osmolality has previously been reported not to have an impact on pain caused by vaccination [115], but keeping osmolality in this range is nevertheless preferred.

Compositions of the invention may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition of the invention will generally be between 5.0 and 7.5, and more typically between 5.0 and 6.0 for optimum stability, or between 6.0 and 7.0. The process of the invention may therefore include a step of adjusting the pH of the bulk vaccine prior to packaging.

Compositions of the invention are preferably sterile.

Compositions of the invention are preferably non-pyrogenic e.g. containing <1 EU (endotoxin unit, a standard measure) per dose, and preferably <0.1 EU per dose.

Compositions of the invention are preferably gluten free.

The pH of any aqueous packaged vaccine materials is preferably between 5 and 8 e.g. between 5.5 and 6.5.

Due to the adsorbed nature of the HBsAg, the final vaccine product may be a suspension with a cloudy appearance. This appearance means that microbial contamination is not readily visible, and so the vaccine preferably contains an antimicrobial agent. This is particularly important when the vaccine is packaged in multidose containers. Preferred antimicrobials for inclusion are 2-phenoxyethanol and thimerosal. It is preferred, however, not to use mercurial preservatives (e.g. thimerosal) during the process of the invention. However, the presence of trace amounts may be unavoidable if the HBsAg was treated with such a preservative before being used to prepare the composition of the invention. For safety, however, it is preferred that the final composition contains less than about 25 ng/ml mercury. More preferably, the final vaccine product contains no detectable thimerosal. This will generally be achieved by removing the mercurial preservative from an antigen preparation prior to its addition in the process of the invention or by avoiding the use of thimerosal during the preparation of the components used to make the composition.

Where a bivalent D-T mixture is used during a process of the invention, it should be free from thimerosal. In some embodiments, the D-T mixture may include 2-phenoxyethanol, but in others it is free from both thimerosal and 2-phenoxyethanol. Where a trivalent D-T-Pw mixture is used during a process of the invention, it can be free from 2-phenoxyethanol, but may include thimerosal.

During manufacture, dilution of components to give desired final concentrations will usually be performed with WFI (water for injection).

The concentration of aluminum phosphate in a composition of the invention, expressed in terms of $Al^{3+}$, is preferably less than 5 mg/ml e.g. $\leq$4 mg/ml, $\leq$3 mg/ml, $\leq$2 mg/ml, $\leq$1 mg/ml, etc.

The concentration of any 3D-MPL in a composition of the invention is preferably less than 200 μg/ml e.g. $\leq$150 μg/ml, $\leq$125 μg/ml, $\leq$110 μg/ml, $\leq$100 μg/ml, etc.

The concentration of HBsAg in a composition of the invention is preferably less than 60 μg/ml e.g. $\leq$55 μg/ml, $\leq$50 μg/ml, $\leq$45 μg/ml, $\leq$40 μg/ml, etc. A concentration of about 20 μg/ml is typical.

The concentration of diphtheria toxoid in a composition of invention is typically at least 50 IU/ml.

The concentration of tetanus toxoid in a composition of the invention is typically at least 100 IU/ml.

The ratio of diphtheria toxoid to tetanus toxoid in compositions of the invention is usually between 2:1 and 3:1 (measured in Lf units), preferably between 2.4:1 and 2.6:1, and is more preferably 2.5:1.

Where cellular pertussis antigen is used, there will typically be at least 8 IU/ml; where acellular antigens are used, there will typically be between 25-75 μg PT, about 25-75 μg FHA and about 10-20 μg pertactin per dose.

The amount of Hib conjugate, measured as saccharide, in compositions of the invention is typically between 10 and 30 μg/ml.

The amount of HAV antigen, measured in EU (Elisa Units), is typically at least 600 EU/ml.

The amount of IPV antigen depends on the strain serotype. For a type 1 virus, a composition typically contains about 80 DU/ml. For a type 2 virus, a composition typically contains about 16 DU/ml. For a type 3 virus, a composition typically contains about 65 DU/ml.

The amount of a meningococcal conjugate, measured as saccharide, in compositions of the invention is typically between 5 and 25 μg/ml for each serogroup.

The amount of a pneumococcal conjugate, measured as saccharide, in compositions of the invention is typically between 2 and 20 μg/ml for each serotype.

Compositions of the invention are preferably administered to patients in 0.5 ml doses. References to 0.5 ml doses will be understood to include normal variance e.g. 0.5 ml±0.05 ml.

The invention can provide bulk material which is suitable for packaging into individual doses, which can then be distributed for administration to patients. Concentrations mentioned above are typically concentrations in final packaged dose, and so concentrations in bulk vaccine may be higher (e.g. to be reduced to final concentrations by dilution).

Compositions of the invention will generally be in aqueous form.

Packaging Compositions of the Invention

After combining the HBsAg and the adjuvants, the processes of the invention may comprise a step of extracting and packaging a 0.5 ml sample of the mixture into a container. For multidose situations, multiple dose amounts will be extracted and packaged together in a single container.

The processes of the invention may comprise the further step of packaging the vaccine into containers for use. Suitable containers include vials and disposable syringes (preferably sterile ones).

Where a composition of the invention is packaged into vials, these are preferably made of a glass or plastic material. The vial is preferably sterilized before the composition is added to it. To avoid problems with latex-sensitive patients, vials are preferably sealed with a latex-free stopper. The vial may include a single dose of vaccine, or it may include more than one dose (a 'multidose' vial) e.g. 10 doses. When using a multidose vial, each dose should be withdrawn with a sterile needle and syringe under strict aseptic conditions, taking care to avoid contaminating the vial contents. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where the composition is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of butyl rubber. If the syringe and needle are packaged separately then the needle is preferably fitted with a butyl rubber shield. Grey butyl rubber is preferred. Preferred syringes are those marketed under the trade name "Tip-Lok"™.

Where a glass container (e.g. a syringe or a vial) is used, then it is preferred to use a container made from a borosilicate glass rather than from a soda lime glass.

After a composition is packaged into a container, the container can then be enclosed within a box for distribution e.g. inside a cardboard box, and the box will be labeled with details of the vaccine e.g. its trade name, a list of the antigens in the vaccine (e.g. 'hepatitis B recombinant', etc.), the presentation container (e.g. 'Disposable Prefilled Tip-Lok Syringes' or '10×0.5 ml Single-Dose Vials'), its dose (e.g. 'each containing one 0.5 ml dose'), warnings (e.g. 'For Adult Use Only' or 'For Pediatric Use Only'), an expiration date, an indication (e.g. 'active immunisation against hepatitis B virus (HBV) infection caused by all known subtypes for patients with renal insufficiency (including pre-haemodialysis and haemodialysis) patients, from the age of 15 years onwards', etc.), a patent number, etc. Each box might contain more than one packaged vaccine e.g. five or ten packaged vaccines (particularly for vials). If the vaccine is contained in a syringe then the package may show a picture of the syringe.

The vaccine may be packaged together (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

The packaged vaccine is preferably stored at between 2° C. and 8° C. It should not be frozen.

Vaccines can be provided in full-liquid form (i.e. where all antigenic components are in aqueous solution or suspension) during manufacture, or they can be prepared in a form where some components are in liquid form and others are in a lyophilized form. Thus a final vaccine can be prepared extemporaneously at the time of use by mixing together two components: (a) a first component comprising aqueous antigens; and (b) a second component comprising lyophilized antigens. The two components are preferably in separate containers (e.g. vials and/or syringes), and the invention provides a kit comprising components (a) and (b). This format is particularly useful for vaccines that include a conjugate component, particularly Hib and/or meningococcal conjugates, as these may be more stable in lyophilized form. Thus conjugates may be lyophilised prior to their use with the invention. Further components may also be added prior to freeze-drying e.g. as stabilizers. Preferred stabilizers for inclusion are lactose, sucrose and mannitol, as well as mixtures thereof e.g. lactose/sucrose mixtures, sucrose/mannitol mixtures, etc. The final vaccine may thus contain lactose and/or sucrose. Using a sucrose/mannitol mixture can speed up the drying process.

Thus the invention provides a process for preparing a two-container combination vaccine, comprising the following steps:
  preparing an aqueous combination vaccine as described above, but wherein the said one or more antigens does not include a conjugated capsular saccharide antigen;
  packaging said combination vaccine in a first container (e.g. a syringe);
  preparing a conjugated capsular saccharide antigen in lyophilised form;
  packaging said lyophilised antigen in a second container (e.g. a vial); and
  packaging the first container and second container together in a kit.

The kit can then be distributed to physicians.

D, T, P and HBsAg components are preferably in liquid form.

Methods of Treatment and Administration of the Vaccine

Compositions of the invention are suitable for administration to human patients, and the invention provides a method of raising an immune response in a patient, comprising the step of administering a composition of the invention to the patient.

The invention also provides a composition of the invention for use in medicine.

The invention also provides the use of (i) HBsAg expressed according to the invention and (ii) one or more non-HBV antigens, in the manufacture of a medicament for administering to a patient.

The invention also provides the use of (i) HBsAg expressed according to the invention and (ii) an adjuvant other than an aluminum hydroxide, in the manufacture of a medicament for administering to a patient. The medicament is preferably a monovalent vaccine. Preferred patient groups for receiving this vaccine are mentioned above.

Immunogenic compositions of the invention are preferably vaccines, for use in the prevention and/or treatment of at least hepatitis B virus infection. Patients who have received compositions of the invention preferably have a serum anti-HBsAg GM titer of ≧500 mIU/ml, measured 6 weeks after the first immunisation. More preferably, the titer is ≧500 mIU/ml, when measured after 12 months.

In order to have full efficacy, a typical immunization schedule for a child may involve administering more than one dose. For example, doses may be at: 0 & 6 months (time 0 being the first dose); at 0, 1, 2 & 6 months; at day 0, day 21 and then a third dose between 6 & 12 months; or at 0, 1, 2, 6 & 12 months.

Compositions of the invention can be administered by intramuscular injection e.g. into the arm or leg Vaccines produced by the invention may be administered to patients at the same time as a separate pneumococcal conjugate vaccine, such as Prevnar™.

Where compositions of the invention include an aluminum-based adjuvant, settling of components may occur during storage. The composition should therefore be shaken prior to administration to a patient. The shaken composition will be a turbid white suspension.

Preferred Vaccines

Specific multivalent immunogenic compositions of the invention include:

A bivalent composition comprising HBsAg and HAV. The vaccine is in aqueous form. It includes both aluminum hydroxide and aluminum phosphate adjuvants. HBsAg is adsorbed to aluminum phosphate. HAV is adsorbed to aluminum hydroxide. Amounts per ml: about 720 ELISA units HAV; about 20 µg HBsAg. Dose: about 1 ml. May be presented in pre-filled syringe.

A pentavalent composition comprising HBsAg, D, T, Pa and IPV. The vaccine is in aqueous form. It includes both aluminum hydroxide and aluminum phosphate adjuvants. HBsAg is adsorbed to aluminum phosphate. D, T and Pa are adsorbed to aluminum hydroxide. Amounts per ml: about 50 Lf diphtheria toxoid; about 20 Lf tetanus toxoid; about 50 µg PT; about 50 µg FHA; about 16 µg pertactin; about 20 µg HBsAg; about 80 DU type 1 poliovirus; about 16 DU type 2 poliovirus; about 64 DU type 3 poliovirus. Dose: about 0.5 ml. May be presented in pre-filled syringe.

A pentavalent composition comprising HBsAg, D, T, Pa and IPV. The vaccine is in aqueous form. It includes both aluminum hydroxide and aluminum phosphate adjuvants. HBsAg is adsorbed to aluminum phosphate. D, T and Pa are adsorbed to aluminum hydroxide. Amounts per ml: at least 60 IU diphtheria toxoid; at least 80 IU tetanus toxoid; about 50 µg PT; about 50 µg FHA; about 16 µg pertactin; about 20 µg HBsAg; about 80 DU type 1 poliovirus; about 16 DU type 2 poliovirus; about 64 DU type 3 poliovirus. Dose: about 0.5 ml. May be presented in pre-filled syringe.

A tetravalent composition comprising HBsAg, D, T and Pw. The components are in aqueous form. It includes both aluminum hydroxide and aluminum phosphate adjuvants. HBsAg is adsorbed to aluminum phosphate. D and T are adsorbed to aluminum hydroxide. The composition includes thimerosal, but preferably does not contain 2-penoxyethanol. Amounts per ml: at least 60 IU diphtheria toxoid; at least 120 IU tetanus toxoid; at least 8 IU Pw; about 20 µg HBsAg. Dose: about 0.5 ml.

A pentavalent composition comprising HBsAg, D, T, Pw and a Hib-T conjugate. The HBsAg, D, T and Pw components are in aqueous form; the Hib-T is lyophilised. It includes both aluminum hydroxide and aluminum phosphate adjuvants. D and T are adsorbed to aluminum hydroxide. HBsAg and Hib-T are adsorbed to aluminum phosphate. The lyophilized Hib-T includes lactose. The aqueous component may include thimerosal. Amounts per ml: at least 60 IU diphtheria toxoid; at least 120 IU tetanus toxoid (plus between 5-25 µg tetanus toxoid as carrier in Hib-T); at least 8 IU Pw; about 20 µg HBsAg; about 5 µg Hib-T, measured as saccharide. Dose: about 0.5 ml.

These compositions can be used separately, or as components of further vaccines. For example, the invention provides a hexavalent composition comprising the pentavalent HBsAg-D-T-Pa-IPV composition described above, plus a lyophilized Hib-T conjugate. The lyophilized Hib-T is preferably not adsorbed to an aluminum salt. The invention also provides a pentavalent composition comprising the tetravalent HBsAg-D-T-Pw composition described above, plus a lyophilized Hib-T conjugate. The invention also provides a heptavalent composition comprising the tetravalent HBsAg-D-T-Pw composition described above, plus a lyophilized mixture of Hib-T conjugate, MenA conjugate and MenC conjugate. The final vaccines can be prepared by reconstituting the lyophilized materials with the aqueous HBsAg-containing materials at the time of use, and the lyophilized and aqueous components are preferably packaged together in a kit, as described above.

A specific monovalent immunogenic composition of the invention is:

HBsAg in combination with an aluminum phosphate adjuvant and a 3D-MPL adjuvant, where the HBsAg and 3D-MPL are both adsorbed to the aluminum phosphate. Amounts per dose: about 20 µg HBsAg, about 50 µg 3D-MPL, about 0.5 mg $Al^{3+}$.

Specific processes of the invention include those comprising the following steps:

Purify HBsAg after expression according to invention; adsorb HBsAg to aluminum phosphate adjuvant; obtain thimerosal-free bivalent D-T mixture with aluminum hydroxide adjuvant; obtain PT, FHA and pertactin for Pa component; obtain IPV antigens, as pooled types 1, 2 and 3, preferably without aluminum salt adjuvant; combine D-T, Pa, IPV and HBsAg, in any order, to give final pentavalent combination; optionally, package into syringe.

Purify HBsAg after expression according to invention; adsorb HBsAg to aluminum phosphate adjuvant; obtain 2-phenoxyethanol-free, thimerosal-containing trivalent D-T-Pw mixture with aluminum hydroxide and aluminum phosphate adjuvants; combine D-T-Pw and HBsAg to give final tetravalent combination; optionally, package into syringe; optionally, package in combination with lyophilized conjugate component(s) e.g. Hib-T, MenA, MenC.

Purify HBsAg after expression according to invention; adsorb HBsAg to aluminum phosphate adjuvant; obtain 2-phenoxyethanol-free, thimerosal-containing trivalent D-T-Pw mixture with aluminum hydroxide and aluminum phosphate adjuvants; obtain lyophilized Hib-T conjugate; combine D-T-Pw and HBsAg to give aqueous tetravalent component; package aqueous tetravalent component into glass vial; package lyophilized Hib-T into glass vial; combine the two vials to be presented in a single kit for reconstitution to give a pentavalent combination vaccine. The glass vials can be type I glass and have rubber butyl stoppers.

Purify HBsAg after expression according to invention; adsorb HBsAg to aluminum phosphate adjuvant; obtain 2-phenoxyethanol-free, thimerosal-containing trivalent D-T-Pw mixture with aluminum hydroxide and aluminum phosphate adjuvants; obtain IPV antigens, as pooled types 1, 2 and 3, preferably without aluminum salt adjuvant; combine D-T-Pw, IPV and HBsAg in any order to give final pentavalent combination; optionally, package into syringe; optionally, package in combination with lyophilized conjugate component(s) e.g. Hib-T, MenA, MenC.

Further components may be added at any stage e.g. sodium chloride, adjuvants, preservatives, etc. These processes can be used e.g. to prepare the vaccines described above.

The different process steps may be performed at substantially the same time, or may be performed separately. They can be performed in the same location or in different locations, even in different countries e.g. HBsAg expression may take place in a different place from lyophilisation of Hib-T conjugate.

Carrier Proteins for Conjugates

Conjugated saccharide antigens include a carrier protein, to which the saccharide is covalently attached, either directly or via a linker. General information on conjugation techniques can be found in reference 116.

Various proteins are known for use as carriers, and preferred carrier proteins are bacterial toxins or toxoids, such as diphtheria toxoid or tetanus toxoid. Other suitable carrier proteins include, but are not limited to, the CRM197 mutant of diphtheria toxin [117-119], the *N. meningitidis* outer membrane protein [120], synthetic peptides [121, 122], heat shock proteins [123,124], pertussis proteins [125,126], cytokines [127], lymphokines [127], hormones [127], growth factors [127], artificial proteins comprising multiple human $CD4^+$ T cell epitopes from various pathogen-derived antigens [128] such as N19 [129], protein D from *H. influenzae [*130,131], pneumococcal surface protein PspA [132], pneumolysin [133], iron-uptake proteins [134], toxin A or B from *C. difficile [*135], *S. agalactiae* proteins [136], etc.

Attachment of a saccharide to a carrier is preferably via a $—NH_2$ group e.g. in the side chain of a lysine residue in a carrier protein, or of an arginine residue. Attachment to —SH groups (e.g. in the side chain of a cysteine) is also possible.

Conjugates with a saccharide:protein ratio (w/w) of between 1:5 (i.e. excess protein) and 5:1 (i.e. excess saccharide) are preferred.

Compositions may include a small amount of free carrier. Ignoring any carrier included as a separate antigen, unconjugated carrier is preferably no more than 5% of the total amount of the carrier protein in the composition as a whole, and more preferably present at less than 2% by weight.

It is possible to include more than one type of carrier protein in a composition e.g. to reduce the risk of carrier suppression.

The carrier protein used for *N. meningitidis* conjugates may be protein D from *H. influenzae*. This protein is described in detail in references 137 & 138, and its use as a carrier protein in conjugates is described in reference 139. The term "protein D" includes fragments of the native full-length protein, as disclosed in reference 139, and also fusion proteins comprising either full-length protein D or these fragments (e.g. a fusion of a fragment of influenza virus NS1 protein and a fragment of protein D). The fragments will retain the ability to convert a T-independent saccharide antigens into a T-dependent antigen when conjugated thereto. Typical fragments will include at least the N-terminal ⅓ of protein D. The protein can conveniently be expressed in *E. coli [*138], and this recombinant material is preferred for use with the invention [139].

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where an antigen is described as being "adsorbed" to an adjuvant, it is preferred that at least 50% (by weight) of that antigen is adsorbed e.g. 50%, 60%, 70%, 80%, 90%, 95%, 98% or more. It is preferred that diphtheria toxoid and tetanus toxoid are both totally adsorbed i.e. none is detectable in supernatant. Total adsorption of HBsAg is also preferred.

It will be appreciated that ionisable groups may exist in the neutral form shown in formulae herein, or may exist in charged form e.g. depending on pH. Thus a phosphate group may be shown as $—P—O—(OH)_2$, this formula is merely representative of the neutral phosphate group, and other charged forms are encompassed by the invention. Similarly, sugar rings can exist in open and closed form and, while closed forms are shown in structural formulae herein, open forms are also encompassed by the invention.

Where animal (and particularly bovine) materials are used in the culture of cells, they should be obtained from sources that are free from transmissible spongiform encephalopathies (TSEs), and in particular free from bovine spongiform encephalopathy (BSE).

SEQUENCE LISTING DETAILS

| ID NO: | DETAILS |
|---|---|
| 1 | Preferred GAPDH promoter nucleotide sequence |
| 2 | SEQ ID NO: 1, followed by a start codon. |
| 3 | Preferred HBsAg amino acid sequence |
| 4 | Preferred HBsAg nucleotide sequence |
| 5 | Known 1061-mer promoter sequence [41] |
| 6 | Known nucleotides downstream of ARG3 stop codon (GI:171076.) |
| 7 | SEQ ID NO: 6, extending 250 nucleotides further back into the coding sequence |
| 8 | Preferred sequence for use downstream of HBsAg coding sequence |
| 9 | SEQ ID NO: 8 with upstream ochre stop codon |
| 10 | Known HBsAg amino acid sequence (CAA84792.1) |
| 11 | TLR adjuvant |
| 12 | TLR adjuvant |
| 13 | Combined sequence with promoter, HBsAg coding and terminator sequences |

MODES FOR CARRYING OUT THE INVENTION

Plasmid Preparation

A plasmid is constructed comprising various elements in the following order: a yeast GAPDH promoter; a HBsAg-coding sequence; a region including a yeast ARG3 transcription terminator; DNA from *E. coli* vector pBR327; yeast DNA with a LEU2 marker; DNA from E. coli vector pBR327; yeast 2μ plasmid sequence; DNA from E. coli vector pBR327. The pBR327 sequences include an ori functional in E. coli. The plasmid is between 14600 and 14700 bp long in total.

The GAPDH promoter sequence includes the following 1060-mer (SEQ ID NO: 1):

aagcttaccagttctcacacggaacaccactaatggacacacattcgaaa tactttgaccctattttcgaggaccttgtcaccttgagcccaagagagcc aagatttaaattttcctatgacttgatgcaaattcccaaagctaataaca tgcaagacacgtacggtcaagaagacatatttgacctcttaacaggttca gacgcgactgcctcatcagtaagacccgttgaaaagaacttacctgaaaa aaacgaatatatactagcgttgaatgttagcgtcaacaacaagaagttta ctgacgcggaggccaaggcaaaaagattccttgattacgtaagggagtta gaatcattttgaataaaaaacacgcttttttcagttcgagtttatcattat caatactgccatttcaaagaatacgtaaataattaatagtagtgattttc ctaactttatttagtcaaaaaattagccttttaattctgctgtaacccgt acatgcccaaaataggggggcgggttacacagaatatataacatcgtaggt gtctgggtgaacagtttattcctggcatccactaaatataatggagcccg cttttttaagctggcatccagaaaaaaaagaatcccagcaccaaaatatt gttttcttcaccaaccatcagttcataggtccattctcttagcgcaacta cagagaacaggggcacaaacaggcaaaaaacgggcacaacctcaatggag tgatgcaacctgcctggagtaaatgatgacacaaggcaattgacccacgc atgtatctatctcattttcttacaccttctattaccttctgctctctctg atttggaaaaagctgaaaaaaaaggttgaaaccagttccctgaaattatt cccctacttgactaataagtatataaagacggtaggtattgattgtaatt ctgtaaatctatttcttaaacttcttaaattctactttatagttagtct tttttttagttttaaaacaccaagaacttagtttcgaataaacacacata aacaaacaaa The HBsAg-coding sequence is as follows (SEQ ID NO: 4), followed by an ochre stop codon:

atggagaacatcacatcaggattcctaggacccctgctcgtgttacaggc ggggttttttcttgttgacaagaatcctcacaataccgcagagtctagact cgtggtggacttctctcaattttctaggggggatcacccgtgtgtcttggc caaaattcgcagtccccaacctccaatcactcaccaacctcctgtcctcc aatttgtcctggttatcgctggatgtgtctgcggcgttttatcatattcc tcttcatcctgctgctatgcctcatcttcttattggttcttctggattat caaggtatgttgcccgtttgtcctctaattccaggatcaacaacaaccaa tacgggaccatgcaaacctgcacgactcctgctcaaggcaactctatgt ttccctcatgttgctgtacaaaacctacggatggaaattgcacctgtatt cccatcccatcgtcctgggctttcgcaaaatacctatgggagtgggcctc agtccgtttctcttggctcagtttactagtgccatttgttcagtggttcg tagggctttcccccactgtttggctttcagctatatggatgatgtggtat tggggggccaagtctgtacagcatcgtgagtccctttataccgctgttacc aattttctttgtctctgggtatacatt This sequence encodes a polypeptide with the following amino acid sequence SEQ ID NO: 3:

MENITSGFLGPLLVLQAGFFLLTRILTIPQSLDSWWTSLNFLGGSPVCLG

QNSQSPTSNHSPTSCPPICPGYRWMCLRRFIIFLFILLLCLIFLLVLLDY

QGMLPVCPLIPGSTTTNTGPCKTCTTPAQGNSMFPSCCCTKPTDGNCTCI

PIPSSWAFAKYLWEWASVRFSWLSLLVPFVQWFVGLSPTVWLSAIWMMWY

WGPSLYSIVSPFIPLLPIFFCLWVYI

The ARG3 sequence includes the following 689-mer sequence (SEQ ID NO: 8), together with additional sequence from the region downstream or ARG3:

cgaattccaagctgaaacaattcaaaggttttcaaatcaatcaagaactt gtctctgtggctgatccaaactacaaatttatgcattgtctgccaagaca tcaagaagaagttagtgatgatgtcttttatggagagcattccatagtct ttgaagaagcagaaaacagattatatgcagctatgtctgccattgatatc tttgttaataataaaggtaatttcaaggacttgaaataatccttctttcg tgttcttaataactaatatataaatacagatatagatgcatgaataatga tatacattgattattttgcaatgtcaattaaaaaaaaaaaatgttagtaa aactatgttacattccaagcaaataaagcacttggttaaacgaaattaac gtttttaagacagccagaccgcggtctaaaaatttaaatatacactgcca acaaattccttcgagttgtccaatttcaccacttttatattttcatcaac ttcagcagattcaaccttctcacatagaacattggaataaacagccttaa caccactttcaagtttgcacagcgtaatatgaggaattttgtttttgacaa cacaaccctttaattttctcattgttttcatcaattatgcatccatcttt atctttagacagttccactacaatagcaatagtttttttc Thus the plasmid includes the following 2430-mer in an expression cassette (SEQ ID NO: 13):

aagcttaccagttctcacacggaacaccactaatggacacacattcgaaa tactttgaccctattttcgaggaccttgtcaccttgagcccaagagagcc aagatttaaattttcctatgacttgatgcaaattcccaaagctaataaca tgcaagacacgtacggtcaagaagacatatttgacctcttaacaggttca gacgcgactgcctcatcagtaagacccgttgaaaagaacttacctgaaaa aaacgaatatatactagcgttgaatgttagcgtcaacaacaagaagttta ctgacgcggaggccaaggcaaaaagattccttgattacgtaagggagtta gaatcattttgaataaaaaacacgcttttttcagttcgagtttatcattat caatactgccatttcaaagaatacgtaaataattaatagtagtgattttc ctaactttatttagtcaaaaaattagccttttaattctgctgtaacccgt acatgcccaaaataggggggcgggttacacagaatatataacatcgtaggt -continued

```
gtctgggtgaacagtttattcctggcatccactaaatataatggagcccg
cttttttaagctggcatccagaaaaaaaaagaatcccagcaccaaaatatt
gttttcttcaccaaccatcagttcataggtccattctcttagcgcaacta
cagagaacaggggcacaaacaggcaaaaaacgggcacaacctcaatggag
tgatgcaacctgcctggagtaaatgatgacacaaggcaattgacccacgc
atgtatctatctcattttcttacaccttctattaccttctgctctctctg
atttggaaaaagctgaaaaaaaaggttgaaaccagttccctgaaattatt
cccctacttgactaataagtatataaagacggtaggtattgattgtaatt
ctgtaaatctatttcttaaacttcttaaattctacttttatagttagtct
ttttttttagttttaaaacaccaagaacttagtttcgaataaacacacata
aacaaacaaaATGgagaacatcacatcaggattcctaggaccccctgctcg
tgttacaggcggggttttttcttgttgacaagaatcctcacaataccgcag
agtctagactcgtggtggacttctctcaattttctaggggatcaccgt
gtgtcttggccaaaattcgcagtccccaacctccaatcactcaccaacct
cctgtcctccaatttgtcctggttatcgctggatgtgtctgcggcgtttt
atcatattcctcttcatcctgctgctatgcctcatcttcttattggttct
tctggattatcaaggtatgttgcccgtttgtcctctaattccaggatcaa
caacaaccaatacgggaccatgcaaaacctgcacgactcctgctcaaggc
aactctatgtttccctcatgttgctgtacaaaacctacggatggaaattg
cacctgtattcccatccatcgtcctgggctttcgcaaaatacctatggg
```

```
agtgggcctcagtccgtttctcttggctcagtttactagtgccatttgtt
cagtggttcgtagggcttttccccactgtttggctttcagctatatggat
gatgtggtattgggggccaagtctgtacagcatcgtgagtccctttatac
cgctgttaccaattttcttttgtctctgggtatacattTAAcgaattcca
agctgaaacaattcaaaggttttcaaatcaatcaagaacttgtctctgtg
gctgatccaaactacaaatttatgcattgtctgccaagacatcaagaaga
agttagtgatgatgtcttttatggagagcattccatagtctttgaagaag
cagaaaacagattatatgcagctatgtctgccattgatatctttgttaat
aataaaggtaatttcaaggacttgaaataatccttctttcgtgttcttaa
taactaatatataaatacagatatagatgcatgaataatgatatacattg
attattttgcaatgtcaattaaaaaaaaaaaatgttagtaaaactatgtt
acattccaagcaaataaagcacttggttaaacgaaattaacgttttttaag
acagccagaccgcggtctaaaaatttaaatatacactgccaacaaattcc
ttcgagttgtccaatttcaccacttttatattttcatcaacttcagcaga
ttcaaccttctcacatagaacattggaataaacagccttaacaccactttt
caagtttgcacagcgtaatatgaggaattttgttttgacaacacaaccct
ttaattttctcattgttttcatcaattatgcatccatctttatctttaga
cagttccactacaatagcaatagtttttttc
```

Sequence Analysis of Plasmid Elements

The GAPDH promoter sequence (SEQ ID NO: 1) was differs from the GAPDH promoter sequence disclosed in reference 41 (SEQ ID NO: 5) at several positions:

```
  0 [AAGCTTACCAGTTCTCACACGGAACACCACTAATGGACACA] a [ATTCGAAATACT
  0 [AAGCTTACCAGTTCTCACACGGAACACCACTAATGGACACA] c [ATTCGAAATACT

54 TTGACCCTATTTTCGAGGACCTTGTCACCTTGAGCCCAAGAGAGCCAAGATTTAAATTTT
 54 TTGACCCTATTTTCGAGGACCTTGTCACCTTGAGCCCAAGAGAGCCAAGATTTAAATTTT

114 CCTATGACTTGATGCAAATTCCCAAAGCTAATAACATGCAAGACACGTACGGTCAAGAAG
114 CCTATGACTTGATGCAAATTCCCAAAGCTAATAACATGCAAGACACGTACGGTCAAGAAG

174 ACATATTTGACCTCTTAAC] t [GGTTCAGACGCGACTGCCTCATCAGTAAGACCCGTT
174 ACATATTTGACCTCTTAAC] a [GGTTCAGACGCGACTGCCTCATCAGTAAGACCCGTT

230 GAAAAGAACTTACCTGAAAAAAACGAATATATACTAGCGTTGAATGTTAGCGTCAACAAC
230 GAAAAGAACTTACCTGAAAAAAACGAATATATACTAGCGTTGAATGTTAGCGTCAACAAC

290 AAGAAGTTTA] a [TGACGCGGAGGCCAAGGCAAAAAGATTCCTTGATTACGTAAGGGA
290 AAGAAGTTTA] c [TGACGCGGAGGCCAAGGCAAAAAGATTCCTTGATTACGTAAGGGA

346 GTTAGAATCATTTTGAATAAAAAACACGCTTTTTCAGTTCGAGTTTATCATTATCAATAC
346 GTTAGAATCATTTTGAATAAAAAACACGCTTTTTCAGTTCGAGTTTATCATTATCAATAC

406 TGCCATTTCAAAGAATACGTAAATAATTAATAGTAGTGATTTTCCTAACTTTATTTAGTC
406 TGCCATTTCAAAGAATACGTAAATAATTAATAGTAGTGATTTTCCTAACTTTATTTAGTC

466 ] . [AAAAATTAGCCTTTTAATTCTGCTGTAACCCGTACATGCCCAAAATAGGGGCGG
466 ] a [AAAAATTAGCCTTTTAATTCTGCTGTAACCCGTACATGCCCAAAATAGGGGCGG

521 GTTACACAGAATATATAACATCGTAGGTGTCTGGGTGAACAGTTTAT] c [CCTGGCAT
522 GTTACACAGAATATATAACATCGTAGGTGTCTGGGTGAACAGTTTAT] t [CCTGGCAT

577 CCACTAAATATAATGCAGC] tcgc. [TTTTAAGCTGGCATCCAGAAAAAAAAAGAATC
578 CCACTAAATATAATGGAGC] ccgct [TTTTAAGCTGGCATCCAGAAAAAAAAAGAATC 632 CCAGCACCAAAATATTGTTTTCTTCACCAACCATCAGTTCATAGGTCCATTCTCTTAGCG
634 CCAGCACCAAAATATTGTTTTCTTCACCAACCATCAGTTCATAGGTCCATTCTCTTAGCG

692 CAACTACAGAGAACAGGGGCACAAACAGGCAAAAAACGGGCACAACCTCAATGGAGTGAT
```

-continued
```
 694 CAACTACAGAGAACAGGGGCACAAACAGGCAAAAAACGGGCACAACCTCAATGGAGTGAT 752 GCAACCTGCCTGGAGTAAATGATGACACAAGGCAATTGACCCACGCATGTATCTATCTCA
 754 GCAACCTGCCTGGAGTAAATGATGACACAAGGCAATTGACCCACGCATGTATCTATCTCA 812 TTTTCTTACACCTTCTATTACCTTCTGCTCTCTCTGATTTGGAAAAAGCTGAAAAAAAAG
 814 TTTTCTTACACCTTCTATTACCTTCTGCTCTCTCTGATTTGGAAAAAGCTGAAAAAAAAG 872 GTTCAAACCAGTTCCCTGAAATTATTCCCCTACTTGACTAATAAGTATATAAAGACGGTA
 874 GTTGAAACCAGTTCCCTGAAATTATTCCCCTACTTGACTAATAAGTATATAAAGACGGTA 932 GGTATTGATTGTAATTCTGTAAATCTATTTCTTAAACTTCTTAAATTCTACTTTTATAGT
 934 GGTATTGATTGTAATTCTGTAAATCTATTTCTTAAACTTCTTAAATTCTACTTTTATAGT 992 TAGTCTTTTTTTTAGTTTTAAAACACCAAGAACTTAGTTTCGAATAAACACACATAAACA
 994 TAGTCTTTTTTTTAGTTTTAAAACACCAAGAACTTAGTTTCGAATAAACACACATAAACA 1052 AACAA] gctt
1054 AACAA] a...
```

SEQ ID NO: 1 was queried against "All GenBank+ EMBL+DDBJ+PDB sequences (but no EST, STS, GSS, environmental samples or phase 0, 1 or 2 HTGS sequences)" on 7 Apr. 2005, with no filtering. The top hit in this search aligns with SEQ ID NO: 1 as follows:

```
>gi|1323342|emb|Z72978.1|SCYGR193C S. cerevisiae chromosome VII reading frame ORF YGR193c
Length = 2262
Score = 2085 bits (1052), Expect = 0.0
Identities = 1058/1060 (99%)
Strand = Plus / Minus Query:    1 aagcttaccagttctcacacggaacaccactaatggacacagattcgaaatactttgacc   60
            |||||||||||||||||||||||||||||||||||||| |||||||||||||||||||||
Sbjct: 1060 aagcttaccagttctcacacggaacaccactaatggacacaaattcgaaatactttgacc 1001

Query:   61 ctatttt cgaggaccttgtcaccttgagcccaagagagccaagatttaaattttcctatg  120
            ||||||||||||||||||||||||||||||||||||||||||||||||||||||||||||
Sbjct: 1000 ctattttcgaggaccttgtcaccttgagcccaagagagccaagatttaaattttcctatg  941

Query:  121 acttgatgcaaattcccaaagctaataacatgcaagacacgtacggtcaagaagacatat  180
            ||||||||||||||||||||||||||||||||||||||||||||||||||||||||||||
Sbjct:  940 acttgatgcaaattcccaaagctaataacatgcaagacacgtacggtcaagaagacatat  881

Query:  181 ttgacctcttaacaggttcagacgcgactgcctcatcagtaagaccc gttgaaaagaact  240
            ||||||||||||||||||||||||||||||||||||||||||||||||||||||||||||
Sbjct:  880 ttgacctcttaacaggttcagacgcgactgcctcatcagtaagacccgttgaaaagaact  821

Query:  241 tacctgaaaaaaacgaatatatactagcgttgaatgttagcgtcaacaacaagaagttta  300
            ||||||||||||||||||||||||||||||||||||||||||||||||||||||||||||
Sbjct:  820 tacctgaaaaaaacgaatatatactagcgttgaatgttagcgtcaacaacaagaagttta  761

Query:  301 gtgacgcggaggccaaggcaaaaagattccttgattacgtaagggagttagaatcatttt  360
            |||||||||||||||||||||||||||||||||||||||||||||||||||||||||||
Sbjct:  760 atgacgcggaggccaaggcaaaaagattccttgattacgtaagggagttagaatcatttt  701

Query:  361 gaataaaaaacacgcttttt cagttcgagtttatcattatcaatactgccatttcaaaga  420
            ||||||||||||||||||||||||||||||||||||||||||||||||||||||||||||
Sbjct:  700 gaataaaaaacacgcttttt cagttcgagtttatcattatcaatactgccatttcaaaga  641

Query:  421 atacgtaaataattaatagtagtgattttcctaactttatttagtcaaaaaattagcctt  480
            ||||||||||||||||||||||||||||||||||||||||||||||||||||||||||||
Sbjct:  640 atacgtaaataattaatagtagtgattttcctaactttatttagtcaaaaaattagcctt  581

Query:  481 ttaattctgctgtaacccgtacatgcccaaaatagggggcgggttacacagaatatataa  540
            ||||||||||||||||||||||||||||||||||||||||||||||||||||||||||||
Sbjct:  580 ttaattctgctgtaacccgtacatgcccaaaatagggggcgggttacacagaatatataa  521

Query:  541 catcgtaggtgtctgggcgaacagtttattcctggcatccactaaatataatggagcccg  600
            |||||||||||||| |||||||||||||||||||||||||||||||||||||||||||||
Sbjct:  520 catcgtaggtgtctgggtgaacagtttattcctggcatccactaaatataatggagcccg  461

Query:  601 cttttt aagctggcatccagaaaaaaaagaatcccagcaccaaaatattgttttcttca  660
            ||||||||||||||||||||||||||||||||||||||||||||||||||||||||||||
Sbjct:  460 cttttt aagctggcatccagaaaaaaaagaatcccagcaccaaaatattgttttcttca  401

Query:  661 ccaaccatcagttcataggtccattctcttagcgcaactacagagaacaggggcacaaac  720
            ||||||||||||||||||||||||||||||||||||||||||||||||||||||||||||
Sbjct:  400 ccaaccatcagttcataggtccattctcttagcgcaactacagagaacaggggcacaaac  341

Query:  721 aggcaaaaacgggcacaacctcaatggagtgatgcaacctgcctggagtaaatgatgac  780
            ||||||||||||||||||||||||||||||||||||||||||||||||||||||||||||
Sbjct:  340 aggcaaaaacgggcacaacctcaatggagtgatgcaacctgcctggagtaaatgatgac  281

Query:  781 acaaggcaattgacccacgcatgtatctatctcatttt cttacaccttctattaccttct 840
            ||||||||||||||||||||||||||||||||||||||||||||||||||||||||||||
Sbjct:  280 acaaggcaattgacccacgcatgtatctatctcatttt cttacaccttctattaccttct 221

Query:  841 gctctctctgatttggaaaaagctgaaaaaaaggttgaaaccagttccctgaaattatt  900
            ||||||||||||||||||||||||||||||||||||||||||||||||||||||||||||
Sbjct:  220 gctctctctgatttggaaaaagctgaaaaaaaggttgaaaccagttccctgaaattatt  161
```

-continued

```
Query:   901 ccctacttgactaataagtatataaagacggtaggtattgattgtaattctgtaaatct  960
             ||||||||||||||||||||||||||||||||||||||||||||||||||||||||||||
Sbjct:   160 ccctacttgactaataagtatataaagacggtaggtattgattgtaattctgtaaatct  101

Query:   961 atttcttaaacttcttaaattctactttt atagttagtcttttttttagtttcaaaacac 1020
             ||||||||||||||||||||||||||||||||||||||||||||||||||||||||||||
Sbjct:   100 atttcttaaacttcttaaattctactttt atagttagtcttttttttagttttaaaacac   41

Query:  1021 caagaacttagtttcgaataaacacacataaacaaacaaa  1060
             ||||||||||||||||||||||||||||||||||||||||
Sbjct:    40 caagaacttagtttcgaataaacacacataaacaaacaaa     1
```

Thus SEQ ID NO: 1 differs at two nucleotides compared to the reverse complement of the nearest match.

The HBsAg coding sequence (SEQ ID NO: 4) was analyzed against GenBank sequences in the same way. SEQ ID NO: 4 differs from the closest database match (AY576426.1) only at nucleotide 350 (A/G). This difference results in a Ser/Asn codon change.

The encoded sequence (SEQ ID NO: 3) was analyzed by BLASTP on 4 Apr. 2005, using the "non-redundant GenBank CDS translations+PDB+SwissProt+PIR+PRF excluding environmental samples" database with no filtering. SEQ ID NO: 3 differs from the closest database matches at amino acid 117, having an Asn residue rather than Ser. The top hit was entry CAA84792.1 (SEQ ID NO: 10):

```
>gi|527444|emb|CAA84792.| surface protein S [Hepatitis B virus]
 gi|7429123|pir||JQ1575 major surface antigen - hepatitis B virus
 Length = 400

Score =  494 bits (1271), Expect = e139
 Identities = 225/226 (99%), Positives = 226/226 (100%)
 Query:   1 MENITSGFLGPLLVLQAGFFLLTRILTIPQSLDSWWTSLNFLGGSPVCLGQNSQSPTSNH   60 SEQ ID NO: 3
             MENITSGFLGPLLVLQAGFFLLTRILTIPQSLDSWWTSLNFLGGSPVCLGQNSQSPTSNH
 Sbjct: 175 MENITSGFLGPLLVLQAGFFLLTRILTIPQSLDSWWTSLNFLGGSPVCLGQNSQSPTSNH  234 SEQ ID NO: 10

Query:  61 SPTSCPPICPGYRWMCLRRFIIFLFILLLCLIFLLVLLDYQGMLPVCPLIPGSTTTNTGP  120
             SPTSCPPICPGYRWMCLRRFIIFLFILLLCLIFLLVLLDYQGMLPVCPLIPGSTTT+TGP
 Sbjct: 235 SPTSCPPICPGYRWMCLRRFIIFLFILLLCLIFLLVLLDYQGMLPVCPLIPGSTTTSTGP  294

Query: 121 CKTCTTPAQGNSMFPSCCCTKPTDGNCTCIPIPSSWAFAKYLWEWASVRFSWLSLLVPFV  180
             CKTCTTPAQGNSMFPSCCCTKPTDGNCTCIPIPSSWAFAKYLWEWASVRFSWLSLLVPFV
 Sbjct: 295 CKTCTTPAQGNSMFPSCCCTKPTDGNCTCIPIPSSWAFAKYLWEWASVRFSWLSLLVPFV  354

Query: 181 QWFVGLSPTVWLSAIWMMWYWGPSLYSIVSPFIPLLPIFFCLWVYI  226
             QWFVGLSPTVWLSAIWMMWYWGPSLYSIVSPFIPLLPIFFCLWVYI
 Sbjct: 355 QWFVGLSPTVWLSAIWMMWYWGPSLYSIVSPFIPLLPIFFCLWVYI  400
```

BLASTN analysis of the downstream sequence from ARG3 (SEQ ID NO: 8) reveals a 100% match with database entry M28301.1, but only over a 683-mer overlap starting at nucleotide 7 of SEQ ID NO: 8. A CLUSTALW alignment of these two sequences, including the 7 nucleotides at the 5' end of SEQ ID NO: 8, is given below:

```
               10        20        30        40        50        60        70
                |         |         |         |         |         |         |
SEQID7  AGAATTTGCGAAACAGGCCAAGCTGAAACAATTCAAAGGTTTTCAAATCAATCAAGAACTTGTCTCTGTG
SEQID8  CGAATT-----------CCAAGCTGAAACAATTCAAAGGTTTTCAAATCAATCAAGAACTTGTCTCTGTG
          *****           ******************************************************

80        90       100       110       120       130       140
                |         |         |         |         |         |         |
SEQID7  GCTGATCCAAACTACAAATTTATGCATTGTCTGCCAAGACATCAAGAAGAAGTTAGTGATGATGTCTTTT
SEQID8  GCTGATCCAAACTACAAATTTATGCATTGTCTGCCAAGACATCAAGAAGAAGTTAGTGATGATGTCTTTT
        **********************************************************************

150       160       170       180       190       200       210
                |         |         |         |         |         |         |
SEQID7  ATGGAGAGCATTCCATAGTCTTTGAAGAAGCAGAAAACAGATTATATGCAGCTATGTCTGCCATTGATAT
SEQID8  ATGGAGAGCATTCCATAGTCTTTGAAGAAGCAGAAAACAGATTATATGCAGCTATGTCTGCCATTGATAT
        **********************************************************************
```

-continued

```
              220       230       240       250       260       270       280
               |         |         |         |         |         |         |
SEQID7  CTTTGTTAATAATAAAGGTAATTTCAAGGACTTGAAATAATCCTTCTTTCGTGTTCTTAATAACTAATAT
SEQID8  CTTTGTTAATAATAAAGGTAATTTCAAGGACTTGAAATAATCCTTCTTTCGTGTTCTTAATAACTAATAT
        **********************************************************************

290       300       310       320       330       340       350
               |         |         |         |         |         |         |
SEQID7  ATAAATACAGATATAGATGCATGAATAATGATATACATTGATTATTTTGCAATGTCAATTAAAAAAAAAA
SEQID8  ATAAATACAGATATAGATGCATGAATAATGATATACATTGATTATTTTGCAATGTCAATTAAAAAAAAAA
        **********************************************************************

360       370       380       390       400       410       420
               |         |         |         |         |         |         |
SEQID7  AATGTTAGTAAAACTATGTTACATTCCAAGCAAATAAAGCACTTGGTTAAACGAAATTAACGTTTTTAAG
SEQID8  AATGTTAGTAAAACTATGTTACATTCCAAGCAAATAAAGCACTTGGTTAAACGAAATTAACGTTTTTAAG
        **********************************************************************

430       440       450       460       470       480       490
               |         |         |         |         |         |         |
SEQID7  ACAGCCAGACCGCGGTCTAAAAATTTAAATATACACTGCCAACAAATTCCTTCGAGTTGTCCAATTTCAC
SEQID8  ACAGCCAGACCGCGGTCTAAAAATTTAAATATACACTGCCAACAAATTCCTTCGAGTTGTCCAATTTCAC
        **********************************************************************

500       510       520       530       540       550       560
               |         |         |         |         |         |         |
SEQID7  CACTTTTATATTTTCATCAACTTCAGCAGATTCAACCTTCTCACATAGAACATTGGAATAAACAGCCTTA
SEQID8  CACTTTTATATTTTCATCAACTTCAGCAGATTCAACCTTCTCACATAGAACATTGGAATAAACAGCCTTA
        **********************************************************************

570       580       590       600       610       620       630
               |         |         |         |         |         |         |
SEQID7  ACACCACTTTCAAGTTTGCACAGCGTAATATGAGGAATTTTGTTTTGACAACACAACCCTTTAATTTTCT
SEQID8  ACACCACTTTCAAGTTTGCACAGCGTAATATGAGGAATTTTGTTTTGACAACACAACCCTTTAATTTTCT
        **********************************************************************

640       650       660       670       680       690       700
               |         |         |         |         |         |         |
SEQID7  CATTGTTTTCATCAATTATGCATCCATCTTTATCTTTAGACAGTTCCACTACAATAGCAATAGTTTTTTC
SEQID8  CATTGTTTTCATCAATTATGCATCCATCTTTATCTTTAGACAGTTCCACTACAATAGCAATAGTTTTTTC
        **********************************************************************
```

HBsAg Expression and Adsorption

The plasmid is used to transform a leu2-3 leu2-112 his3 can1-11 strain of *S. cerevisiae* yeast (DC5). The yeast are grown in a synthetic medium containing purified amino acids (but omitting leucine), vitamins, and suitable salts. Expressed HBsAg is purified by a process involving cell recovery, precipitation, ultrafiltration, gel permeation, ion exchange, ultracentrifugation and desalting.

The purified antigen is non-glycosylated and can be seen in the form of substantially-spherical particles (average diameter ~20 nm).

A suspension of aluminum phosphate in isotonic saline is mixed with the purified HBsAg concentrate. After adjusting the pH to between 5.2 and 6.0, the mixture is left at room temperature for a day, with stirring. Adsorption of antigen to adjuvant takes place over this time.

Monovalent Vaccine

For making a monovalent vaccine, 3D-MPL is added to the adsorbed HBsAg, and dilution to give a final HBsAg concentration of 20 μg/ml is achieved using water for injection and sterile saline. This bulk vaccine is then packaged into individual doses, either in vials or into disposable syringes.

Multivalent Vaccine

For making a combination vaccine, a DTPw antigen mixture is obtained from Chiron Behring in Marburg, Germany. This mixture is mixed with adsorbed HBsAg to give a tetravalent vaccine product. The tetravalent product can be used on its own, or can be used to reconstitute either (a) a lyophilized Hib-T conjugate that is adsorbed to an aluminum phosphate adjuvant, or (b) a trivalent mixture of lyophilized conjugates from Hib, MenA and MenC.

It will be understood that the invention has been described by way of example only and modifications may be made whilst remaining within the scope and spirit of the invention.

REFERENCES (THE CONTENTS OF WHICH ARE HEREBY INCORPORATED BY REFERENCE)

[1] *Vaccines*. (eds. Plotkin & Orenstein). 4th edition, 2004, ISBN: 0-7216-9688-0.
[2] Desombere et al. (2002) *Vaccine* 20:2597-602.
[3] Cooper et al. (2004) *J Clin Immunol* 24:693-701.
[4] Pasek et al. (1979) *Nature* 282:575-9.
[5] MacKay et al. (1981) *PNAS USA* 78:4510-4.
[6] Fujisawa et al. (1983) *Nucleic Acids Res* 11:4645-54.
[7] Dubois et al. (1980) *PNAS USA* 77:4549-53.
[8] Hirschman et al. (1980) *PNAS USA* 77:5507-11.
[9] Liu et al. (1982) *DNA* 1:213-21.
[10] Valenzuela et al. (1982) *Nature* 298:347-50.
[11] Harford et al. (1983) *Dev Biol Stand* 54:125-30.
[12] McAleer et al. (1984) *Nature* 307:178-80.
[13] Smith et al. (2002) *Biotechnol Prog* 18:538-50.
[14] Shulga et al. (2004) *Biochemistry* (*Mosc*) 69:1158-64.
[15] Valdes et al. (2004) *BBRC* 310:742-7.
[16] Smith et al. (2003) *Vaccine* 21:4011-21.
[17] Sojikul et al. (2003) *PNAS USA* 100:2209-14.
[18] Smith et al. (2002) *Biotechnol Bioeng* 80:812-22.
[19] Kong et al. (2001) *PNAS USA* 98:11539-44.
[20] Richter et al. (2000) *Nature Biotechnol* 18:1167-71.
[21] Kapusta et al. (1999) *FASEB J* 13:1796-9.
[22] Mason et al. (1992) *PNAS USA* 89:11745-9.
[23] Huang et al. (2005) *Vaccine* 23:1851-8.
[24] Thanvala et al. (2005) *PNAS USA* 102:3378-82.
[25] Valdés et al. (2003) *BBRC* 310:742-7.
[26] Hardy et al. (2000) *J Biotechnol* 17:157-67.
[27] Lepetec et al. (2003) *Vaccine* 21:4481-5.
[28] Heijtink et al. (2002) *Vaccine* 20:2191-6.
[29] Vanlandschoot et al. (2003) *J Med Virol* 70:513-9.
[30] Desombere et al. (1998) *Tissue Antigens* 51:593-604.
[31] McDermott et al. (1997) *Tissue Antigens*. 50:8-14.

[32] Blitz et al. (1998) *J Clin Microbiol* 36:648-51.
[33] Teles et al. (2002) *J Med Virol* 68:41-9.
[34] *MMWR* Apr. 12, 1996/45(14); 285-9.
[35] Teles et al. (1999) *Artif Organs* 23):1074-8.
[36] Lewis-Ximeneza et al. (2001) *Nephron* 87:19-26.
[37] Holland & Holland (1979) *J. Biol. Chem.* 254:5466-74.
[38] Holland & Holland (1979) *J. Biol. Chem.* 254:9839-45.
[39] Holland & Holland (1980) *J. Biol. Chem.* 255:2596-605.
[40] Holland et al. (1983) *J. Biol. Chem.* 258:5291-9.
[41] European patent 0460716; U.S. Pat. No. 5,349,059.
[42] Crabeel et al. (1983) *Proc Natl Acad Sci USA* 78:5026-30.
[43] Cabezón et al. (1984) *Proc Natl Acad Sci USA* 81:6594-8.
[44] van der Straten et al. (1986) *DNA* 5:129-36.
[45] Harford et al. (1987) *Postgraduate Medical Journal* 63(suppl 2):65-70.
[46] Ludwig & Bruschi (1991) *Plasmid* 25:81-95.
[47] U.S. Pat. No. 4,683,294.
[48] WO03/066094.
[49] Kandimalla et al. (2003) *Nucleic Acids Research* 31:2393-2400.
[50] WO02/26757.
[51] WO99/62923.
[52] Krieg (2003) *Nature Medicine* 9:831-835.
[53] McCluskie et al. (2002) *FEMS Immunology and Medical Microbiology* 32:179-185.
[54] WO98/40100.
[55] U.S. Pat. No. 6,207,646.
[56] U.S. Pat. No. 6,239,116.
[57] U.S. Pat. No. 6,429,199.
[58] Kandimalla et al. (2003) *Biochemical Society Transactions* 31 (part 3):654-658.
[59] Blackwell et al. (2003) *J Immunol* 170:4061-4068.
[60] Krieg (2002) *Trends Immunol* 23:64-65.
[61] WO01/95935.
[62] Kandimalla et al. (2003) *BBRC* 306:948-953.
[63] Bhagat et al. (2003) *BBRC* 300:853-861.
[64] WO03/035836.
[65] Johnson et al. (1999) *Bioorg Med Chem Lett* 9:2273-2278.
[66] Evans et al. (2003) *Expert Rev Vaccines* 2:219-229.
[67] Baldridge et al. (2002) *J Endotoxin Res* 8:453-8.
[68] Persing et al. (2002) *Trends Immunol* 10:S32-S37.
[69] Boland et al. (2004) *Vaccine* 23:316-20.
[70] U.S. Pat. No. 6,013,264.
[71] UK patent application 2220211.
[72] Myers et al. (1990) pages 145-156 of *Cellular and molecular aspects of endotoxin reactions.*
[73] Ulrich (2000) Chapter 16 (pages 273-282) of *Vaccine Adjuvants: Preparation Methods and Research Protocols* (Volume 42 of *Methods in Molecular Medicine* series). ISBN: 1-59259-083-7. Ed. O'Hagan.
[74] Johnson et al. (1999) *J Med Chem* 42:4640-9.
[75] Baldrick et al. (2002) *Regulatory Toxicol Pharmacol* 35:398-413.
[76] WO 94/21292.
[77] Sesardic et al. (2001) *Biologicals* 29:107-22.
[78] NIBSC code: 98/560.
[79] Module 1 of WHO's *The immunological basis for immunization series* (Galazka).
[80] NIBSC code: 69/017.
[81] NIBSC code: DIFT.
[82] Sesardic et al. (2002) *Biologicals* 30:49-68.
[83] NIBSC code: 98/552.
[84] NIBSC code: TEFT.
[85] NIBSC code: 66/303.
[86] Rappuoli et al. (1991) *TIBTECH* 9:232-238.
[87] WO96/40242.
[88] Module 6 of WHO's *The immunological basis for immunization series* (Robertson)
[89] Jones (2001) *Curr Opin Investig Drugs* 2:47-49.
[90] Costantino et al. (1992) *Vaccine* 10:691-8.
[91] Lieberman et al. (1996) *JAMA* 275:1499-503.
[92] WO02/058737.
[93] WO03/007985.
[94] Rennels et al. (2002) *Pediatr Infect Dis J* 21:978-979.
[95] Campbell et al. (2002) *J Infect Dis* 186:1848-1851.
[96] *W.H.O. Tech. Rep. Ser.* 594:51, 1976.
[97] Watson (2000) *Pediatr Infect Dis J* 19:331-332.
[98] Rubin (2000) *Pediatr Clin North Am* 47:269-285, v.
[99] Jedrzejas (2001) *Microbiol Mol Biol Rev* 65:187-207.
[100] Zielen et al. (2000) *Infect. Immun.* 68:1435-1440.
[101] Darkes & Plosker (2002) *Paediatr Drugs* 4:609-630.
[102] Berkower et al. (2004) *Virology* 321(1):75-86.
[103] Eckhart et al. (1996) *J Gen Virol* 77:2001-8.
[104] von Brunn et al. (1991) *Vaccine* 9(7):477-84.
[105] Vreden et al. (1991) *Am J Trop Med Hyg* 45(5):533-8.
[106] Moelans et al. (1995) *Mol Biochem Parasitol* 72(1-2):179-92.
[107] Stoute et al. (1997) *N Engl J Med* 336(2):86-91.
[108] Wunderlich & del Portillo (2000) *Mol Med* 6(3):238-45.
[109] U.S. Pat. No. 5,928,902
[110] WO93/10152.
[111] *Vaccine Design: The Subunit and Adjuvant Approach* (eds. Powell & Newman) Plenum Press 1995 (ISBN 0-306-44867-X).
[112] EP-A-0833662.
[113] U.S. Pat. No. 6,756,040.
[114] WO02/00249.
[115] Nony et al. (2001) *Vaccine* 27:3645-51.
[116] *Conjugate Vaccines* (eds. Cruse et al.) ISBN 3805549326, particularly vol. 10:48-114.
[117] Anonymous (January 2002) *Research Disclosure*, 453077.
[118] Anderson (1983) *Infect Immun* 39(1):233-238.
[119] Anderson et al. (1985) *J Clin Invest* 76(1):52-59.
[120] EP-A-0372501.
[121] EP-A-0378881.
[122] EP-A-0427347.
[123] WO93/17712
[124] WO94/03208.
[125] WO98/58668.
[126] EP-A-0471177.
[127] WO91/01146
[128] Falugi et al. (2001) *Eur J Immunol* 31:3816-24.
[129] Baraldo et al. (2004) *Infect Immun* 72:4884-87.
[130] EP-A-0594610.
[131] WO00/56360.
[132] WO02/091998.
[133] Kuo et al. (1995) *Infect Immun* 63:2706-13.
[134] WO01/72337.
[135] WO00/61761.
[136] WO2004/041157.
[137] WO91/18926 and U.S. Pat. Nos. 5,858,677, 5,888,517, 5,989,828, 6,025,484 & 6,139,846
[138] Janson et al. (1991) *Infect Immun* 59:119-25.
[139] WO00/56360.

The invention claimed is:

1. A process for preparing a multivalent immunogenic composition, comprising the steps of:
   (a) preparing a HBV component by purifying HBsAg after expression in a *S. cerevisiae* host carrying a plasmid having a HBsAg coding sequence, wherein the plasmid includes: (1) an upstream promoter from a glyceraldehyde-3-phosphate dehydrogenase gene, for controlling expression of the HBsAg coding sequence; and (2) an ARG3 transcription terminator downstream of the HBsAg coding sequence;
   (b) preparing at least one immunogenic non-HBV component; and
   (c) mixing the HBV and non-HBV components to give the multivalent composition,
   wherein the upstream promoter comprises the nucleotide sequence of SEQ ID NO:1.

2. A process for preparing a monovalent immunogenic composition, comprising the steps of:
   (a) preparing a HBV component by purifying HBsAg after expression in a *S. cerevisiae* host carrying a plasmid having a HBsAg coding sequence, wherein the plasmid includes: (1) an upstream promoter from a glyceraldyde-3-phosphate dehydrogenase gene, for controlling expression of the HBsAg coding sequence; and (2) an ARG3 transcription terminator downstream of the HBsAg coding sequence; and
   (b) combining the HBsAg with an adjuvant to give the immunogenic composition, provided that the adjuvant is not an aluminum hydroxide adjuvant,
   wherein the upstream promoter comprises the nucleotide sequence of SEQ ID NO:1.

3. A process for preparing a monovalent immunogenic composition, comprising the steps of:
   (a) preparing a HBV component by purifying HBsAg after expression in a *S. cerevisiae* host carrying a plasmid having a HBsAg coding sequence, wherein the plasmid includes: (1) an upstream promoter from a glyceraldyde-3-phosphate dehydrogenase gene, for controlling expression of the HBsAg coding sequence; and (2) an ARG3 transcription terminator downstream of the HBsAg coding sequence; and
   (b) combining the HBsAg with an adjuvant to give the immunogenic composition, provided that the adjuvant does not consist solely of an aluminum salt, wherein the upstream promoter comprises the nucleotide sequence of SEQ ID NO:1.

4. The process of claim 2, wherein the adjuvant comprises a mixture of an aluminum phosphate adjuvant and a 3D-MPL adjuvant.

5. The process of claim 4, wherein the 3D-MPL and the HBsAg are both adsorbed to the aluminum phosphate.

6. The process of claim 2, wherein the monovalent immunogenic composition includes polysorbate 20 or phosphatidylinositol.

7. The process of claim 2, wherein the plasmid also includes: (3) a LEU2 selection marker; (4) a 2μ plasmid sequence; and (5) an origin of replication functional in *Escherichia coli*.

8. The process of claim 7, wherein the *S. cerevisiae* host is auxotrophic for leucine, but wherein the plasmid LEU2 marker allows the host to grow in the absence of a leucine source.

9. The process of claim 2, wherein SEQ ID NO: 1 is followed directly by a start codon for the HBsAg.

10. The process of claim 2, wherein the HBsAg the amino acid sequence of SEQ ID NO: 3.

11. The process of claim 2, wherein the HBsAg is encoded in the plasmid by the nucleotide sequence of SEQ ID NO: 4.

12. The process of claim 11, wherein SEQ ID NO: 4 is followed directly by an ochre stop codon.

13. The process of claim 2, wherein the ARG3 terminator comprises the nucleotide sequence of SEQ ID NO: 8.

14. The process of claim 13, wherein SEQ ID NO: 8 is immediately downstream of the stop codon of the HBsAg coding sequence.

15. The process of claim 2, wherein the composition has an osmolality of between 200 mOsm/kg and 400 mOsm/kg.

16. A plasmid comprising:
(1) a HBsAg coding sequence encoding the amino acid sequence of SEQ ID NO: 3;
(2) a promoter from a glyceraldehyde-3-phosphate dehydrogenase gene, upstream of and for controlling expression of the HBsAg coding sequence, wherein the promoter comprises the nucleotide sequence of SEQ ID NO: 1; and
(3) an ARG3 transcription terminator downstream of the HBsAg coding sequence, wherein the terminator comprises the nucleotide sequence of SEQ ID NO: 8.

17. The plasmid of claim 16, having between 14,500 and 15,000 base pairs.

18. A recombinant yeast carrying the plasmid of claim 16.

19. The process of claim 3, wherein the adjuvant comprises a mixture of an aluminum phosphate adjuvant and a 3D-MPL adjuvant.

20. The process of claim 19, wherein the 3D-MPL and the HBsAg are both adsorbed to the aluminum phosphate.

21. The process of claim 3, wherein the monovalent immunogenic composition includes polysorbate 20 or phosphatidylinositol.

22. The process of claim 1, wherein the non-HBV component comprises an antigen selected from the group consisting of: a diphtheria toxoid, a tetanus toxoid, a cellular pertussis antigen, an acellular pertussis antigen, a hepatitis A virus antigen, a conjugated *Haemophilus influenzae* type b capsular saccharide, an inactivated poliovirus, a conjugated *Neisseria meningitidis* serogroup C capsular saccharide, a conjugated *Neisseria meningitidis* serogroup A capsular saccharide, a conjugated *Neisseria meningitidis* serogroup W135 capsular saccharide and a conjugated *Neisseria meningitidis* serogroup Y capsular saccharide.

23. The process of claim 22, wherein the non-HBV component comprises an acellular pertussis antigen.

24. The process of claim 1, wherein the ARG3 terminator comprises the nucleotide sequence of SEQ ID NO:8 and/or the HBsAg comprises the amino acid sequence of SEQ ID NO:3.

25. The process of claim 2, wherein the ARG3 terminator comprises the nucleotide sequence of SEQ ID NO:8 and/or the HBsAg comprises the amino acid sequence of SEQ ID NO:3.

26. The process of claim 3, wherein the ARG3 terminator comprises the nucleotide sequence of SEQ ID NO:8 and/or the HBsAg comprises the amino acid sequence of SEQ ID NO:3.

27. The process of claim 1, wherein the multivalent immunogenic composition includes polysorbate 20 or phosphatidylinositol.

28. The process of claim 1, wherein the plasmid also includes: (3) a LEU2 selection marker; (4) a 2μ plasmid sequence; and (5) an origin of replication functional in *Escherichia coli*.

29. The process of claim 28, wherein the *S. cerevisiae* host is auxotrophic for leucine, but wherein the plasmid LEU2 marker allows the host to grow in the absence of a leucine source.

30. The process of claim 1, wherein SEQ ID NO: 1 is followed directly by a start codon for the HBsAg.

31. The process of claim 1, wherein the HBsAg is encoded in the plasmid by the nucleotide sequence of SEQ ID NO: 4.

32. The process of claim 31, wherein SEQ ID NO: 4 is followed directly by an ochre stop codon.

33. The process of claim 24, wherein SEQ ID NO: 8 is immediately downstream of the stop codon of the HBsAg coding sequence.

* * * * *

SEQUENCE LISTING

<160> NUMBER OF SEQ ID NOS: 15

<210> SEQ ID NO 1
<211> LENGTH: 1060
<212> TYPE: DNA
<213> ORGANISM: Saccharomyces cerevisiae

<400> SEQUENCE: 1

| | | |
|---|---|---|
| aagcttacca gttctcacac ggaacaccac taatggacac acattcgaaa tactttgacc | 60 |
| ctattttcga ggaccttgtc accttgagcc aagagagcc aagatttaaa ttttcctatg | 120 |
| acttgatgca aattcccaaa gctaataaca tgcaagacac gtacggtcaa gaagacatat | 180 |
| ttgacctctt aacaggttca gacgcgactg cctcatcagt aagacccgtt gaaaagaact | 240 |
| tacctgaaaa aaacgaatat atactagcgt tgaatgttag cgtcaacaac aagaagttta | 300 |
| ctgacgcgga ggccaaggca aaagattcc ttgattacgt aagggagtta gaatcatttt | 360 |
| gaataaaaaa cacgcttttt cagttcgagt ttatcattat caatactgcc atttcaaaga | 420 |
| atacgtaaat aattaatagt agtgattttc ctaactttat ttagtcaaaa aattagcctt | 480 |
| ttaattctgc tgtaacccgt acatgcccaa ataggggc gggttacaca gaatatataa | 540 |
| catcgtaggt gtctgggtga acagtttatt cctggcatcc actaaatata atggagcccg | 600 |
| cttttaagc tggcatccag aaaaaaaag aatcccagca ccaaaatatt gttttcttca | 660 |
| ccaaccatca gttcataggt ccattctctt agcgcaacta cagagaacag gggcacaaac | 720 |
| aggcaaaaaa cgggcacaac ctcaatggag tgatgcaacc tgcctggagt aaatgatgac | 780 |
| acaaggcaat tgacccacgc atgtatctat ctcattttct tacaccttct attaccttct | 840 |
| gctctctctg atttggaaaa agctgaaaaa aaaggttgaa accagttccc tgaaattatt | 900 |
| cccctacttg actaataagt atataaagac ggtaggtatt gattgtaatt ctgtaaatct | 960 |
| atttcttaaa cttcttaaat tctacttta tagttagtct ttttttagt tttaaaacac | 1020 |
| caagaactta gtttcgaata acacacata aacaaacaaa | 1060 |

<210> SEQ ID NO 2
<211> LENGTH: 1063
<212> TYPE: DNA
<213> ORGANISM: Saccharomyces cerevisiae

<400> SEQUENCE: 2

| | | |
|---|---|---|
| aagcttacca gttctcacac ggaacaccac taatggacac acattcgaaa tactttgacc | 60 |
| ctattttcga ggaccttgtc accttgagcc aagagagcc aagatttaaa ttttcctatg | 120 |
| acttgatgca aattcccaaa gctaataaca tgcaagacac gtacggtcaa gaagacatat | 180 |
| ttgacctctt aacaggttca gacgcgactg cctcatcagt aagacccgtt gaaaagaact | 240 |
| tacctgaaaa aaacgaatat atactagcgt tgaatgttag cgtcaacaac aagaagttta | 300 |
| ctgacgcgga ggccaaggca aaagattcc ttgattacgt aagggagtta gaatcatttt | 360 |
| gaataaaaaa cacgcttttt cagttcgagt ttatcattat caatactgcc atttcaaaga | 420 |
| atacgtaaat aattaatagt agtgattttc ctaactttat ttagtcaaaa aattagcctt | 480 |
| ttaattctgc tgtaacccgt acatgcccaa ataggggc gggttacaca gaatatataa | 540 |
| catcgtaggt gtctgggtga acagtttatt cctggcatcc actaaatata atggagcccg | 600 |
| cttttaagc tggcatccag aaaaaaaag aatcccagca ccaaaatatt gttttcttca | 660 |
| ccaaccatca gttcataggt ccattctctt agcgcaacta cagagaacag gggcacaaac | 720 |

```
aggcaaaaaa cgggcacaac ctcaatggag tgatgcaacc tgcctggagt aaatgatgac    780
acaaggcaat tgacccacgc atgtatctat ctcattttct tacaccttct attaccttct    840
gctctctctg atttggaaaa agctgaaaaa aaaggttgaa accagttccc tgaaattatt    900
cccctacttg actaataagt atataaagac ggtaggtatt gattgtaatt ctgtaaatct    960
atttcttaaa cttcttaaat tctacttttta tagttagtct ttttttttagt tttaaaacac   1020 caagaactta gtttcgaata aacacacata aacaaacaaa atg                      1063
```

<210> SEQ ID NO 3
<211> LENGTH: 226
<212> TYPE: PRT
<213> ORGANISM: Hepatitis B virus

<400> SEQUENCE: 3

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Asn Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225
```

<210> SEQ ID NO 4
<211> LENGTH: 678
<212> TYPE: DNA
<213> ORGANISM: Hepatitis B virus

<400> SEQUENCE: 4

```
atggagaaca tcacatcagg attcctagga ccccctgctcg tgttacaggc ggggttttttc    60 ttgttgacaa gaatcctcac aataccgcag agtctagact cgtggtggac ttctctcaat   120
tttctagggg gatcacccgt gtgtcttggc caaaattcgc agtccccaac ctccaatcac   180
tcaccaacct cctgtcctcc aatttgtcct ggttatcgct ggatgtgtct gcggcgtttt   240
```

```
atcatattcc tcttcatcct gctgctatgc ctcatcttct tattggttct tctggattat      300
caaggtatgt tgcccgtttg tcctctaatt ccaggatcaa caacaaccaa tacgggacca      360
tgcaaaacct gcacgactcc tgctcaaggc aactctatgt ttccctcatg ttgctgtaca      420
aaacctacgg atggaaattg cacctgtatt cccatcccat cgtcctgggc tttcgcaaaa      480
tacctatggg agtgggcctc agtccgtttc tcttggctca gtttactagt gccatttgtt      540
cagtggttcg tagggctttc ccccactgtt tggctttcag ctatatggat gatgtggtat      600
tgggggccaa gtctgtacag catcgtgagt ccctttatac cgctgttacc aattttcttt      660
tgtctctggg tatacatt                                                   678

<210> SEQ ID NO 5
<211> LENGTH: 1061
<212> TYPE: DNA
<213> ORGANISM: Saccharomyces cerevisiae

<400> SEQUENCE: 5
aagcttacca gttctcacac ggaacaccac taatggacac aaattcgaaa tactttgacc       60
ctattttcga ggaccttgtc accttgagcc aagagagcc aagatttaaa ttttcctatg      120
acttgatgca aattcccaaa gctaataaca tgcaagacac gtacggtcaa gaagacatat      180
ttgacctctt aactggttca gacgcgactg cctcatcagt aagacccgtt gaaaagaact      240
tacctgaaaa aaacgaatat atactagcgt tgaatgttag cgtcaacaac aagaagttta      300
atgacgcgga ggccaaggca aaagattcc ttgattacgt aagggagtta gaatcatttt      360
gaataaaaaa cacgcttttt cagttcgagt ttatcattat caatactgcc atttcaaaga      420
atacgtaaat aattaatagt agtgattttc ctaactttat ttagtcaaaa attagccttt      480
taattctgct gtaacccgta catgcccaaa ataggggcg ggttacacag aatatataac      540
atcgtaggtg tctgggtgaa cagtttatcc ctggcatcca ctaaatataa tggagctcgc      600
ttttaagctg gcatccagaa aaaaaagaa tcccagcacc aaaatattgt tttcttcacc      660
aaccatcagt tcataggtcc attctcttag cgcaactaca gagaacaggg gcacaaacag      720
gcaaaaaacg ggcacaacct caatggagtg atgcaacctg cctggagtaa atgatgacac      780
aaggcaattg acccacgcat gtatctatct cattttctta caccttctat taccttctgc      840
tctctctgat ttggaaaaag ctgaaaaaaa aggttgaaac cagttccctg aaattattcc      900
cctacttgac taataagtat ataaagacgg taggtattga ttgtaattct gtaaatctat      960
ttcttaaact tcttaaattc tacttttata gttagtcttt tttttagttt taaaacacca    1020
agaacttagt ttcgaataaa cacacataaa caaacaagct t                       1061

<210> SEQ ID NO 6
<211> LENGTH: 450
<212> TYPE: DNA
<213> ORGANISM: Saccharomyces cerevisiae

<400> SEQUENCE: 6
tccttctttc gtgttcttaa taactaatat ataaatacag atatagatgc atgaataatg       60
atatacattg attattttgc aatgtcaatt aaaaaaaaaa aatgttagta aaactatgtt      120
acattccaag caaataaagc acttggttaa acgaaattaa cgttttttaag acagccagac      180 cgcggtctaa aaatttaaat atacactgcc aacaaattcc ttcgagttgt ccaatttcac      240
cacttttata ttttcatcaa cttcagcaga ttcaaccttc tcacatagaa cattggaata      300
aacagcctta acaccacttt caagtttgca cagcgtaata tgaggaattt tgttttgaca      360
```

```
acacaaccct ttaattttct cattgttttc atcaattatg catccatctt tatctttaga    420
cagttccact acaatagcaa tagtttttc                                      450
```

<210> SEQ ID NO 7
<211> LENGTH: 700
<212> TYPE: DNA
<213> ORGANISM: Saccharomyces cerevisiae

<400> SEQUENCE: 7

```
agaatttgcg aaacaggcca agctgaaaca attcaaaggt tttcaaatca atcaagaact     60
tgtctctgtg gctgatccaa actacaaatt tatgcattgt ctgccaagac atcaagaaga    120
agttagtgat gatgtctttt atggagagca ttccatagtc tttgaagaag cagaaaacag    180
attatatgca gctatgtctg ccattgatat ctttgttaat aataaaggta atttcaagga    240
cttgaaataa tccttctttc gtgttcttaa taactaatat ataaatacag atatagatgc    300
atgaataatg atatacattg attattttgc aatgtcaatt aaaaaaaaaa aatgttagta    360
aaactatgtt acattccaag caaataaagc acttggttaa cgaaattaa cgttttaag     420 acagccagac cgcggtctaa aaatttaaat atacactgcc aacaaattcc ttcgagttgt    480
ccaatttcac cactttatata ttttcatcaa cttcagcaga ttcaaccttc tcacatagaa    540
cattggaata aacagcctta acaccacttt caagtttgca cagcgtaata tgaggaattt    600
tgttttgaca acacaaccct ttaattttct cattgttttc atcaattatg catccatctt    660
tatctttaga cagttccact acaatagcaa tagtttttc                           700
```

<210> SEQ ID NO 8
<211> LENGTH: 689
<212> TYPE: DNA
<213> ORGANISM: Saccharomyces cerevisiae

<400> SEQUENCE: 8

```
cgaattccaa gctgaaacaa ttcaaaggtt ttcaaatcaa tcaagaactt gtctctgtgg     60
ctgatccaaa ctacaaattt atgcattgtc tgccaagaca tcaagaagaa gttagtgatg    120
atgtctttta tggagagcat tccatagtct ttgaagaagc agaaaacaga ttatatgcag    180
ctatgtctgc cattgatatc tttgttaata ataaaggtaa tttcaaggac ttgaaataat    240
ccttctttcg tgttcttaat aactaatata taaatacaga tatagatgca tgaataatga    300
tatacattga ttattttgca atgtcaatta aaaaaaaaa atgttagtaa aactatgtta    360
cattccaagc aaataaagca cttggttaaa cgaaattaac gttttaaga cagccagacc    420 gcggtctaaa aatttaaata tacactgcca acaaattcct tcgagttgtc caatttcacc    480
acttttatat tttcatcaac ttcagcagat tcaaccttct cacatagaac attggaataa    540
acagccttaa caccactttc aagtttgcac agcgtaatat gaggaatttt gttttgacaa    600
cacaaccctt taattttctc attgttttca tcaattatgc atccatcttt atctttagac    660
agttccacta caatagcaat agtttttc                                       689
```

<210> SEQ ID NO 9
<211> LENGTH: 692
<212> TYPE: DNA
<213> ORGANISM: Saccharomyces cerevisiae

<400> SEQUENCE: 9

```
taacgaattc caagctgaaa caattcaaag gttttcaaat caatcaagaa cttgtctctg     60
tggctgatcc aaactacaaa tttatgcatt gtctgccaag acatcaagaa gaagttagtg    120
```

```
atgatgtctt ttatggagag cattccatag tctttgaaga agcagaaaac agattatatg    180
cagctatgtc tgccattgat atctttgtta ataataagg taatttcaag gacttgaaat     240
aatccttctt tcgtgttctt aataactaat atataaatac agatatagat gcatgaataa    300
tgatatacat tgattatttt gcaatgtcaa ttaaaaaaaa aaaatgttag taaaactatg    360
ttacattcca agcaaataaa gcacttggtt aaacgaaatt aacgttttta agacagccag    420
accgcggtct aaaaatttaa atatacactg ccaacaaatt ccttcgagtt gtccaatttc    480 accacttta tattttcatc aacttcagca gattcaacct tctcacatag aacattggaa     540
taaacagcct taacaccact ttcaagtttg cacagcgtaa tatgaggaat tttgttttga    600
caacacaacc ctttaatttt ctcattgttt tcatcaatta tgcatccatc tttatcttta    660
gacagttcca ctacaatagc aatagttttt tc                                  692
```

<210> SEQ ID NO 10
<211> LENGTH: 226
<212> TYPE: PRT
<213> ORGANISM: Hepatitis B virus

<400> SEQUENCE: 10

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225
```

<210> SEQ ID NO 11
<211> LENGTH: 6
<212> TYPE: DNA
<213> ORGANISM: Artificial Sequence
<220> FEATURE:

<223> OTHER INFORMATION: CpG adjuvant sequence

<400> SEQUENCE: 11 gtcgtt                                                                          6

<210> SEQ ID NO 12
<211> LENGTH: 6
<212> TYPE: DNA
<213> ORGANISM: Artificial Sequence
<220> FEATURE:
<223> OTHER INFORMATION: CpG adjuvant sequence

<400> SEQUENCE: 12 ttcgtt                                                                          6

<210> SEQ ID NO 13
<211> LENGTH: 2430
<212> TYPE: DNA
<213> ORGANISM: Artificial Sequence
<220> FEATURE:
<223> OTHER INFORMATION: CpG adjuvant sequence

<400> SEQUENCE: 13
aagcttacca gttctcacac ggaacaccac taatggacac acattcgaaa tactttgacc      60
ctatttcga ggaccttgtc accttgagcc caagagagcc aagatttaaa ttttcctatg     120
acttgatgca aattcccaaa gctaataaca tgcaagacac gtacggtcaa gaagacatat     180
ttgacctctt aacaggttca gacgcgactg cctcatcagt aagacccgtt gaaaagaact     240
tacctgaaaa aaacgaatat atactagcgt tgaatgttag cgtcaacaac aagaagttta     300
ctgacgcgga ggccaaggca aaagattcc ttgattacgt aagggagtta gaatcatttt     360
gaataaaaaa cacgcttttt cagttcgagt ttatcattat caatactgcc atttcaaaga     420
atacgtaaat aattaatagt agtgattttc taactttat ttagtcaaaa aattagcctt     480
ttaattctgc tgtaacccgt acatgcccaa aataggggc gggttacaca gaatatataa     540
catcgtaggt gtctgggtga acagtttatt cctggcatcc actaaatata atggagcccg     600
cttttaagc tggcatccag aaaaaaaag aatcccagca ccaaaatatt gttttcttca     660
ccaaccatca gttcataggt ccattctctt agcgcaacta cagagaacag gggcacaaac     720
aggcaaaaaa cgggcacaac ctcaatggag tgatgcaacc tgcctggagt aaatgatgac     780
acaaggcaat tgacccacgc atgtatctat ctcatttct acaccttct attaccttct     840
gctctctctg atttggaaaa agctgaaaaa aaaggttgaa accagttccc tgaaattatt     900
cccctacttg actaataagt atataaagac ggtaggtatt gattgtaatt ctgtaaatct     960
attttcttaaa cttcttaaat tctactttta tagttagtct tttttttagt tttaaaacac    1020
caagaactta gttcgaata acacacata aacaaacaaa atggagaaca tcacatcagg    1080
attcctagga ccccctgctcg tgttacaggc ggggttttc ttgttgacaa gaatcctcac    1140
aataccgcag agtctagact cgtggtggac ttctctcaat tttctagggg gatcacccgt    1200
gtgtcttggc caaaattcgc agtccccaac ctccaatcac tcaccaacct cctgtcctcc    1260
aatttgtcct ggttatcgct ggatgtgtct gcggcgtttt atcatattcc tcttcatcct    1320
gctgctatgc ctcatcttct tattggttct tctggattat caaggtatgt tgcccgtttg    1380
tcctctaatt ccaggatcaa caacaaccaa tacgggacca tgcaaaacct gcacgactcc    1440
tgctcaaggc aactctatgt ttccctcatg ttgctgtaca aaacctacgg atggaaattg    1500
cacctgtatt cccatcccat cgtcctgggc tttcgcaaaa tacctatggg agtgggcctc    1560

-continued

```
agtccgtttc tcttggctca gtttactagt gccatttgtt cagtggttcg tagggctttc      1620
ccccactgtt tggctttcag ctatatggat gatgtggtat tggggggccaa gtctgtacag     1680 catcgtgagt cccttatac cgctgttacc aattttcttt tgtctctggg tatacattta       1740
acgaattcca agctgaaaca attcaaaggt tttcaaatca atcaagaact tgtctctgtg      1800
gctgatccaa actacaaatt tatgcattgt ctgccaagac atcaagaaga agttagtgat     1860
gatgtctttt atgagagca ttccatagtc tttgaagaag cagaaaacag attatatgca      1920
gctatgtctg ccattgatat ctttgttaat aataaggta atttcaagga cttgaaataa      1980
tccttctttc gtgttcttaa taactaatat ataaatacag atatagatgc atgaataatg     2040
atatacattg attattttgc aatgtcaatt aaaaaaaaaa aatgttagta aaactatgtt     2100
acattccaag caaataaagc acttggttaa acgaaattaa cgttttttaag acagccagac    2160 cgcggtctaa aaatttaaat atacactgcc aacaaattcc ttcgagttgt ccaatttcac     2220
cacttttata ttttcatcaa cttcagcaga ttcaaccttc tcacatagaa cattggaata    2280
aacagcctta acaccacttt caagtttgca cagcgtaata tgaggaattt tgttttgaca    2340
acacaaccct ttaattttct cattgttttc atcaattatg catccatctt tatctttaga   2400
cagttccact acaatagcaa tagtttttttc                                    2430
```

```
<210> SEQ ID NO 14
<211> LENGTH: 4
<212> TYPE: PRT
<213> ORGANISM: Plasmodium falciparum

<400> SEQUENCE: 14

Asn Ala Asn Pro
1

<210> SEQ ID NO 15
<211> LENGTH: 423
<212> TYPE: PRT
<213> ORGANISM: Artificial Sequence
<220> FEATURE:
<223> OTHER INFORMATION: RTS antigen

<400> SEQUENCE: 15

Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Ala
65                  70                  75                  80

Asn Pro Asn Lys Asn Asn Gln Gly Asn Gly Gln Gly His Asn Met Pro
                85                  90                  95

Asn Asp Pro Asn Arg Asn Val Asp Glu Asn Ala Asn Ala Asn Ala Val
            100                 105                 110

Lys Asn Asn Asn Glu Glu Pro Ser Asp Lys His Ile Glu Gln Tyr
        115                 120                 125

Leu Lys Lys Ile Lys Asn Ser Ile Ser Thr Glu Trp Ser Pro Cys Ser
    130                 135                 140

Val Thr Cys Gly Asn Gly Ile Gln Val Arg Ile Lys Pro Gly Ser Ala
145                 150                 155                 160
```

```
Asn Lys Pro Lys Asp Glu Leu Asp Tyr Glu Asn Asp Ile Glu Lys Lys
            165                 170                 175
Ile Cys Lys Met Glu Lys Cys Ser Ser Val Phe Asn Val Val Asn Ser
            180                 185                 190
Arg Pro Val Thr Asn Met Glu Asn Ile Thr Ser Gly Phe Leu Gly Pro
            195                 200                 205
Leu Leu Val Leu Gln Ala Gly Phe Phe Leu Leu Thr Arg Ile Leu Thr
            210                 215                 220
Ile Pro Gln Ser Leu Asp Ser Trp Trp Thr Ser Leu Asn Phe Leu Gly
225                 230                 235                 240
Gly Ser Pro Val Cys Leu Gly Gln Asn Ser Gln Ser Pro Thr Ser Asn
            245                 250                 255
His Ser Pro Thr Ser Cys Pro Pro Ile Cys Pro Gly Tyr Arg Trp Met
            260                 265                 270
Cys Leu Arg Arg Phe Ile Ile Phe Leu Phe Ile Leu Leu Leu Cys Leu
            275                 280                 285
Ile Phe Leu Leu Val Leu Leu Asp Tyr Gln Gly Met Leu Pro Val Cys
            290                 295                 300
Pro Leu Ile Pro Gly Ser Thr Thr Thr Asn Thr Gly Pro Cys Lys Thr
305                 310                 315                 320
Cys Thr Thr Pro Ala Gln Gly Asn Ser Met Phe Pro Ser Cys Cys Cys
            325                 330                 335
Thr Lys Pro Thr Asp Gly Asn Cys Thr Cys Ile Pro Ile Pro Ser Ser
            340                 345                 350
Trp Ala Phe Ala Lys Tyr Leu Trp Glu Trp Ala Ser Val Arg Phe Ser
            355                 360                 365
Trp Leu Ser Leu Leu Val Pro Phe Val Gln Trp Phe Val Gly Leu Ser
            370                 375                 380
Pro Thr Val Trp Leu Ser Ala Ile Trp Met Met Trp Tyr Trp Gly Pro
385                 390                 395                 400
Ser Leu Tyr Ser Ile Val Ser Pro Phe Ile Pro Leu Leu Pro Ile Phe
            405                 410                 415
Phe Cys Leu Trp Val Tyr Ile
            420
```